(12) United States Patent
Foster et al.

(10) Patent No.: US 12,279,899 B2
(45) Date of Patent: *Apr. 22, 2025

(54) STERILIZABLE COVER

(71) Applicant: RAMPART IC, LLC, Birmingham, AL (US)

(72) Inventors: Robert Evans Foster, Birmingham, AL (US); Lloyd Guyton Bowers Cooper, Birmingham, AL (US); William Thomas Livingston, Birmingham, AL (US); Foster D Phillips, Birmingham, AL (US)

(73) Assignee: RAMPART IC, LLC, Birmingham, AL (US)

( * ) Notice: Subject to any disclaimer, the term of this patent is extended or adjusted under 35 U.S.C. 154(b) by 584 days.

This patent is subject to a terminal disclaimer.

(21) Appl. No.: 17/604,060

(22) PCT Filed: Apr. 17, 2020

(86) PCT No.: PCT/US2020/028825
§ 371 (c)(1),
(2) Date: Oct. 15, 2021

(87) PCT Pub. No.: WO2020/214992
PCT Pub. Date: Oct. 22, 2020

(65) Prior Publication Data
US 2022/0218295 A1 Jul. 14, 2022

Related U.S. Application Data

(63) Continuation of application No. 16/083,393, filed as application No. PCT/US2018/046318 on Aug. 10, 2018, now Pat. No. 11,207,039.
(Continued)

(51) Int. Cl.
*A61B 6/10* (2006.01)
*G21F 3/00* (2006.01)

(52) U.S. Cl.
CPC ............... *A61B 6/107* (2013.01); *G21F 3/00* (2013.01)

(58) Field of Classification Search
CPC .................................. A61B 6/107; G21F 3/00
See application file for complete search history.

(56) References Cited

U.S. PATENT DOCUMENTS

| | | |
|---|---|---|
| 3,984,696 A | 10/1976 | Collica et al. |
| 4,254,341 A | 3/1981 | Herr et al. |

(Continued)

FOREIGN PATENT DOCUMENTS

| | | |
|---|---|---|
| DE | 102014215448 B3 | 12/2015 |
| JP | 2001-120543 A | 5/2001 |

(Continued)

OTHER PUBLICATIONS

Office Action received for European Patent Application No. 18908271.2, mailed on Nov. 29, 2023, 05 pages.
(Continued)

*Primary Examiner* — Sean M Luck
(74) *Attorney, Agent, or Firm* — Nicholas J. Landau; Maynard Nexsen PC

(57) ABSTRACT

A radiation shield assembly is described, configured to block radiation emanating from a radiation source from reaching a user. Two shields are supported by a support arm, and are configured to rotate and translate relative to one another about the support arm's longitudinal axis. This allows the shield to be easily configured and reconfigured as necessary to visualize various parts of a patient's body via radiography. Sterile coverings are provided to ensure asepsis during a surgical procedure.

56 Claims, 12 Drawing Sheets

Related U.S. Application Data

(60) Provisional application No. 62/835,943, filed on Apr. 18, 2019, provisional application No. 62/544,468, filed on Aug. 11, 2017.

(56) References Cited

U.S. PATENT DOCUMENTS

| | | |
|---|---|---|
| 4,280,056 A | 7/1981 | Renshaw |
| 4,581,538 A | 4/1986 | Lenhart |
| D300,945 S | 5/1989 | Fleming et al. |
| 4,923,162 A | 5/1990 | Fleming et al. |
| 4,965,456 A | 10/1990 | Huettenrauch et al. |
| 5,006,718 A | 4/1991 | Lenhart |
| 5,015,864 A | 5/1991 | Maleki |
| 5,090,044 A | 2/1992 | Kobayashi |
| 5,417,225 A | 5/1995 | Rubenstein et al. |
| 5,981,964 A | 11/1999 | McAuley et al. |
| 6,325,538 B1 | 12/2001 | Heesch |
| 6,448,571 B1 | 9/2002 | Goldstein |
| 6,703,632 B1 | 3/2004 | Macklis et al. |
| 7,276,716 B1 | 10/2007 | Munro, III |
| 7,331,712 B2 | 2/2008 | Fischer et al. |
| 7,391,042 B2 | 6/2008 | Goldstein |
| 7,465,947 B2 | 12/2008 | Magram |
| 7,608,847 B2 | 10/2009 | Rees |
| 7,638,784 B2 | 12/2009 | Fox et al. |
| 7,829,873 B2 | 11/2010 | Fox et al. |
| 7,973,299 B2 | 7/2011 | Rees |
| 8,143,607 B2 | 3/2012 | Teodorescu |
| 8,378,326 B2 | 2/2013 | Hunt |
| 8,399,871 B2 | 3/2013 | Beyar et al. |
| 8,439,564 B2 | 5/2013 | Belson et al. |
| 8,598,554 B2 | 12/2013 | Rees |
| 8,683,928 B2 | 4/2014 | Anderson |
| 8,716,687 B2 | 5/2014 | Goldstein et al. |
| 9,349,492 B1 | 5/2016 | Ganus |
| D772,414 S | 11/2016 | Ballsieper |
| 9,877,688 B1 | 1/2018 | Colling |
| 10,441,231 B2 | 10/2019 | Wilson et al. |
| 11,045,155 B2 | 6/2021 | Lemer |
| 11,191,495 B2 | 12/2021 | Wilson et al. |
| 11,207,039 B2 | 12/2021 | Foster et al. |
| 11,666,290 B2 | 6/2023 | Wilson et al. |
| 12,053,312 B2 | 8/2024 | Wilson et al. |
| 2004/0045557 A1 | 3/2004 | Lee et al. |
| 2007/0252095 A1 | 11/2007 | Magram |
| 2010/0319713 A1 | 12/2010 | Byers et al. |
| 2011/0174997 A1 | 7/2011 | Rees |
| 2012/0049093 A1 | 3/2012 | Costea |
| 2012/0132217 A1 | 5/2012 | Rees |
| 2012/0241652 A1 | 9/2012 | Jeschke |
| 2012/0256092 A1 | 10/2012 | Zingerman |
| 2013/0320246 A1 | 12/2013 | Beck |
| 2014/0048730 A1 | 2/2014 | Niedzielski et al. |
| 2015/0272519 A1 | 10/2015 | Buchmeyer |
| 2015/0335297 A1 | 11/2015 | Mogul et al. |
| 2016/0027540 A1 | 1/2016 | Gordon et al. |
| 2016/0029980 A1 | 2/2016 | Osherov et al. |
| 2016/0038365 A1 | 2/2016 | Conner et al. |
| 2016/0220199 A1 | 8/2016 | Gordon |
| 2017/0119324 A1 | 5/2017 | Wilson et al. |
| 2019/0063665 A1 | 2/2019 | LeCote |
| 2022/0071576 A1 | 3/2022 | Foster et al. |
| 2022/0243864 A1 | 8/2022 | Foster et al. |

FOREIGN PATENT DOCUMENTS

| | | |
|---|---|---|
| JP | 2009-541712 A | 11/2009 |
| JP | 2010-230311 A | 10/2010 |
| KR | 101081895 | 11/2011 |
| KR | 10-1913840 B1 | 12/2018 |
| WO | 2018/109380 A1 | 6/2018 |
| WO | 2019216934 A2 | 11/2019 |
| WO | 2020163773 A1 | 8/2020 |
| WO | 2020/214992 A1 | 10/2020 |

OTHER PUBLICATIONS

Notice of Refusal for Japanese Patent Application No. 2021-561838, mailed Nov. 17, 2023, 10 Pages including English Translation.

Examination Report received for Australian Patent Application No. 2018422761, mailed on May 15, 2023, 04 pages.

Office Action received for Canadian Patent Application No. 3072454, mailed on Jul. 21, 2023, 04 pages.

Office Action received for European Patent Application No. 18908271.2, mailed on May 9, 2022, 05 pages.

First Office Action received for Japanese Patent Application No. 2020-530444, mailed on Jun. 21, 2022, 14 pages including English translation.

Second Office Action received for Japanese Patent Application No. 2020-530444, mailed on Nov. 24, 2022, 14 pages including English translation.

Decision of Dismissal of Amendment received for Japanese Patent Application No. 2020-530444, mailed on Apr. 25, 2023, 15 pages including English translation.

International Preliminary Report on Patentability received for International Patent Application No. PCT/US2018/046318, mailed on Feb. 20, 2022, 10 pages.

International Search Report and Written Opinion received for International Patent Application No. PCT/US2018/046318, mailed on Nov. 12, 2019, 13 pages.

International Preliminary Report on Patentability received for International Patent Application No. PCT/US2020/028825, mailed on Oct. 28, 2021, 08 pages.

International Search Report and Written Opinion received for International Patent Application No. PCT/US2020/028825, mailed on Aug. 5, 2020, 10 pages.

Search Report received for Japanese Patent Application No. 2020-530444, mailed on Jun. 15, 2022, 24 pages including English translation.

Search Report & Written Opinion received for Singapore patent Application No. 11202108590W, Completed on Apr. 21, 2023, 11 pages.

International Preliminary Report on Patentability received for International Application No. PCT/US2020/017309, mailed on Aug. 19, 2021, 10 pages.

First Substantive Examination Report received for Saudi Arabia Application No. 521422707, mailed on Jun. 24, 2023, 18 pages including English translation.

Office Action received for Indian patent Application No. 202147040405, mailed on Apr. 18, 2023, 10 pages.

ASTM F3094 (ASTM International "Standard Test Method for Determining Protection Provided by X-ray Shielding Garments Used in Medical X-ray Fluoroscopy from Sources of Scattered X-Rays" ASTM vol. 11.03 Occupational Health and Safety; Protective Clothing (2017).

IEC 61331-1 (International Electrotechnical Commission, "Protective devices against diagnostic medical X-radiation—Part 1: Determination of attenuation properties of materials" (2014).

Aadco Medical, Inc. "Overhead Barriers" obtained from world wide web Dec. 29, 2016; http://www.aadcbmed.com/products/barriers_shields/overhead_barriers; pp. 1-4.

Kenex Co. Lower body x-ray shield 312/E-010; obtained from world wide web Dec. 29, 2016; http://kenex.co.uk/products/x-ray-shielding/x-ray-table-mounted-shields/lower-body-x-ray . . . ; pp. 1-3.

Kenex Co. "Overhead ceiling mounted shield 350" obtained from world wide web Dec. 29, 2016; http://kenex.co.uk/products/x-ray-shielding/overhead-suspended-shields-lamps/overhead . . . ; pp. 1-3.

Fattal, Peter et al. "A Novel Complete Radiation Protection System Eliminates Physician Radiation Exposure and Leaded Aprons" Catheterization and Cardiovascular Interventions 81:11-16 (2013) pp. 1-6.

De La Hera, German "International Search Report and Written Opinion—International Application No. PCT/US2020/017309" Apr. 20, 2020; pp. 1-15.

(56) References Cited

OTHER PUBLICATIONS

Strubel, Christine "International Preliminary Report on Patentability and Written Opinion" European Patent Office; Feb. 11, 2020; pp. 1-9.
Extended European Search Report received for European Patent Application No. 23196608.6, mailed on Dec. 11, 2023, 09 pages.
Office Action received for European Patent Application No. 20725007.7, mailed on Mar. 1, 2024, 4 Pages.
Office Action received for Australian Patent Application No. 2018422761, mailed on Jan. 29, 2024, 03 pages.
Office Action received for Australian Patent Application No. 2018422761, mailed on Feb. 12, 2024, 02 pages.
Office Action received for Canadian Patent Application No. 3072454, mailed on Feb. 7, 2024, 03 pages.
Office Action received for Canadian Patent Application No. 3129066, mailed on Jan. 22, 2024, 04 pages.
Office Action received for European Patent Application No. 20710657.6, mailed on Jan. 15, 2024, 6 Pages.
Notice of Refusal for Japanese Patent Application No. 2021-545836, mailed Mar. 28, 2024, 10 Pages including English Translation.
Office Action received for European Patent Application No. 20710657.6, mailed on Aug. 2, 2024, 05 pages.
Notice of Reasons for Refusal for Japanese Patent Application No. 2021-561838, mailed May 9, 2024, 06 Pages including English Translation.
Notice of Reasons for Refusal for Japanese Patent Application No. 2023-137479, mailed Apr. 30, 2024, 15 Pages including English Translation.
Notice of Reasons for Refusal for Japanese Patent Application No. 2023-137479, mailed Aug. 8, 2024, 06 Pages including English Translation.

STERILIZABLE COVER

CROSS-REFERENCE TO RELATED APPLICATIONS

This is a national stage of PCT/US20/28825, filed on 17 Apr. 2020 (pending). PCT/US20/28825 claims priority to U.S. Patent Application No. 62/835,943, filed on 18 Apr. 2019, which is incorporated herein by reference in its entirety. This is a continuation-in-part of U.S. patent application Ser. No. 16/083,393, filed 7 Sep. 2018 (pending). U.S. patent application Ser. No. 16/083,393 is a national stage of PCT/US18/46318, filed 10 Aug. 2018. PCT/US18/46318 claims priority to U.S. Patent Application No. 62/544,468, filed 11 Aug. 2017.

BACKGROUND

Field

The present disclosure relates generally to radiation protection devices, and specifically to devices to protect medical personnel from radiological hazards in the operating room.

Background

Recent Improvements in electronics and robotics have enabled surgeons to use noninvasive microsurgical techniques to replace numerous open Incision techniques. When the site of surgical Intervention is not open to the operating room, the site must still be visualized in order to adequately guide and control the Instruments. This can be accomplished by radiological monitoring, the most common example of which is X-ray monitoring. During the procedure an X-ray generator is positioned on one side of the patient to emit X-rays to the surgical site (this is generally below the patient, although the position of the X-ray generator can be varied as necessary). An X-ray Intensifier is positioned to receive the emitted X-rays after they have passed through the surgical site, to convey image data to a monitor or other means to present a visual image to the surgeon.

Although these microsurgical techniques represent a vast improvement over previous open body techniques in terms of trauma to the patient, recovery time, and risk of Infection, the constant radiological monitoring exposes everyone involved to more radiation than was required using the old techniques. This is a minor concern for the patient, who is likely to undergo only a small number of such surgeries in a lifetime. However, the professional medical staff who perform these procedures have much more frequent exposure, and the cumulative exposure could easily exceed safe limits unless the staff are somehow protected.

Previous attempts to solve these problems have serious limitations. Placing heavy shielding around the patient can block the radiation from reaching the medical staff. However, the medical staff still need access to the patient's body, so complete shielding is impractical; because the human body is transparent to X-rays ("radiolucent"), X-rays can shine through the patient's body and expose the medical staff. Any surgery carries with it a risk of life-threatening complications that would require the medical staff to have immediate access to the patient's body. Heavy shields around the patient's body are bulky and difficult to move, which can prevent emergency access by the medical staff to the patient in such a situation.

Another attempt to protect medical staff during such procedures has involved worn shielding, or basically radiation "armor." These have taken the form of lead vests, lead skirts, lead thyroid collars, leaded acrylic face shields, leaded acrylic glasses, and "zero gravity" leaded suits. Radiation armor has a serious disadvantage: it must be of significant mass to block X-rays (generally containing lead, a very dense metal), and it is heavy to wear. Wearing heavy radiation armor rapidly fatigues even a physically fit wearer, and with chronic use can cause orthopedic disorders. When using radiation armor to protect medical staff from X-rays, one health hazard is simply being exchanged for another.

Glasses and face shields by themselves might be of a manageable weight, but alone they protect only a tiny portion of the body.

"Zero gravity" suits are leaded body suits that are suspended by a rigid metal frame. The frame is mounted on some supporting structure, such as the floor or ceiling. As a result the wearer does not support the suit with his or her body. This type of suspended armor has additional drawbacks. It leaves the wearer's hands and lower arms uncovered and unprotected to allow the wearer to engage in fine manual work. It limits the wearer's range of bodily movement to movements that can be accommodated by the frame, often preventing the wearer from bending over or sitting. They use a static face shield that prevents the wearer from bringing anything close to the face, for example for visual scrutiny. Suspended armor systems are extremely expensive due to their complexity and due to material costs.

Another form of radiation armor is the mobile "cabin," that is a radiopaque box on wheels in which the user stands. The user is able to push the cabin from place to place while inside. The cabin has arm ports at a certain height and a visually transparent portion at a certain height. As a result the user's hands and face cannot be repositioned or reoriented much, for example to stand or lean over. It also uses a static face shield that prevents the wearer from bringing anything close to the face, for example for visual scrutiny.

There is therefore a need in the art for a means to shield medical staff from X-rays to which a patient must be exposed that does not encumber the user's body, allows access to the patient's body, and can be rapidly reconfigured if necessary.

SUMMARY

The present disclosure describes a radiation shield assembly that addresses the problems described above by interposing a barrier between an operating area and an area containing medical personnel. Working in conjunction with the shield curtain hanging below the operating table, the shield assembly significantly reduces the radiation that reaches the personnel area both directly from the radiation generator and indirectly through the patient's radiolucent body, allows access to the patient's body, allows complete freedom of movement on the part of the user, and can be easily reconfigured as needed. The shield assembly generally comprises two shield structures supported by a support member such as a mast or suspension arm. Each shield structure has at least one generally vertical shield, and the two vertical shields can be rotated relative to one another about the longitudinal axis of the support member and translated relative to one another about the longitudinal axis of the support member.

In a first aspect a radiation shield assembly is provided, configured to block radiation emanating from a radiation source. In the first aspect the assembly comprises supporting means to support the assembly; first shielding means to block radiation from the source in a first approximately vertical plane, fastened to the supporting means, and comprising an appendage opening dimensioned to allow a human appendage to pass through the first shielding means; and second shielding means to block radiation from the source in a second approximately vertical plane, fastened to the supporting means to allow the second shielding means to translate and rotate along an approximately vertical axis relative to the first shielding means.

A second aspect of the radiation shield assembly is provided, said second aspect comprising: a support arm constructed to support at least the majority of the weight of the shield assembly, the support arm having a longitudinal axis; a first generally planar vertical shield fastened to the support arm, and having an opening proximate to a lower end dimensioned to admit a human appendage; a second generally planar vertical shield translatably and rotationally connected to the support arm to rotate about and translate along an axis that is approximately parallel to the longitudinal axis of the support arm; wherein the first vertical shield, first horizontal shield, second vertical shield, second horizontal shield, and lower vertical shield are all radiopaque.

In a third aspect a system for shielding a user from a bottom-mounted X-ray generator while said user attends to a prostrate patient positioned above the X-ray generator is provided, the system comprising: a table constructed to support the patient, the table having a longitudinal axis and a transverse axis; the X-ray generator positioned below the table; an image intensifier positioned above the table to receive X-rays projected from the X-ray generator; a radiopaque curtain shield extending downwardly from the table on at least a first side of the table; and a radiation shield assembly comprising a support arm constructed to support the weight of the shield assembly and having a generally vertical longitudinal axis, a first shield assembly fastened to the support arm, comprising a first generally planar vertical shield, positioned proximate to the first side of the table and approximately parallel to the longitudinal axis of the table and an opening in the first vertical shield positioned above the table to allow the patient's arm to pass through the opening; and a second shield assembly rotatably and translationally fastened to the support arm to allow the second shield assembly to rotate and translate about an axis approximately parallel to the longitudinal axis of the support arm, the second shield assembly comprising a second generally planar vertical shield positioned above the table; wherein the second vertical shield may be rotated about its axis to be approximately orthogonal to the longitudinal axis of the table or to be approximately parallel to the longitudinal axis of the table.

In a fourth aspect, a radiation shield assembly configured to block radiation emanating from a radiation source is provided, the assembly comprising: a support arm constructed to support at least the majority of the weight of the shield assembly, the support arm having a longitudinal axis; a first generally planar vertical shield fastened to the support arm via a first radiopaque joint; and a second generally planar vertical shield translatably and rotationally connected to the support arm via a second radiopaque joint to rotate about and translate along an axis that is approximately parallel to the longitudinal axis of the support arm.

In a fifth aspect, a radiography method is provided, comprising: positioning any of the radiation shield assemblies above between a patient and a user, such that an appendage of the patient extends through an appendage opening in the shield assembly; inserting a medical device into vasculature of the appendage; and irradiating the patient using a radiation generator positioned such that radiation passes at least partially through the patient while being blocked from reaching the user by the shield assembly.

In any of the above aspects a sterile covering may be present on one or more of the shields or shielding means.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

DETAILED DESCRIPTION

A. Definitions

Figure 1:
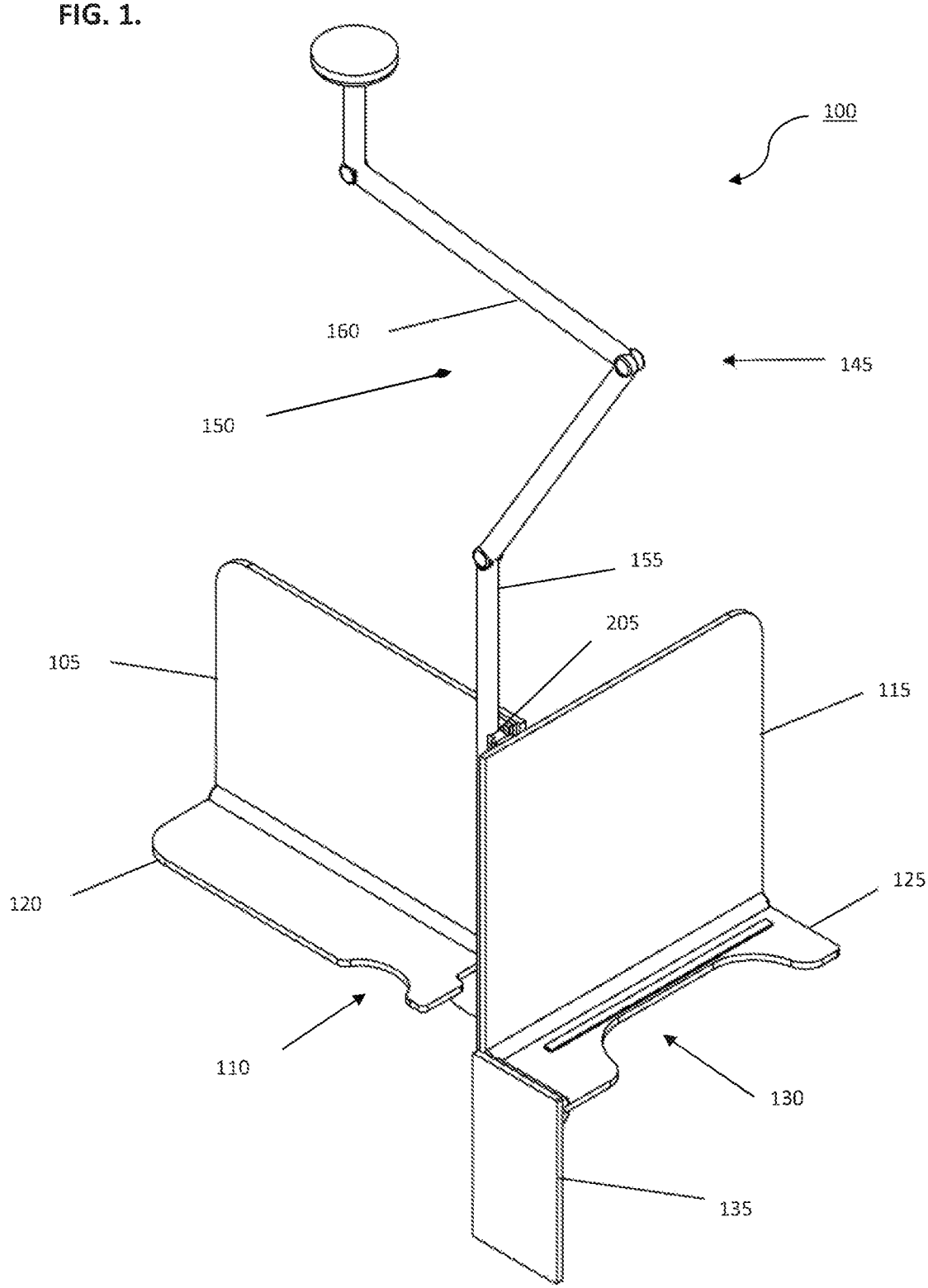
FIG. 1. An embodiment of the shield assembly showing the first and second vertical shields orthogonal to one another, in which the second vertical shield is lowered.

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well known functions or constructions may not be described in detail for brevity or clarity.

The terms "about" and "approximately" shall generally mean an acceptable degree of error or variation for the quantity measured given the nature or precision of the measurements. Typical, exemplary degrees of error or variation are within 20 percent (%), preferably within 10%, and more preferably within 5% of a given value or range of values. For example, the terms "approximately parallel" or "approximately vertical" refer to an angle within an acceptable degree of error or variation from true parallel or vertical, such as within 45, 25, 20, 15, 10, or 1° of true parallel or vertical. Numerical quantities given in this description are approximate unless stated otherwise, meaning that the term "about" or "approximately" can be Inferred when not expressly stated. Claimed numerical quantities are exact unless stated otherwise.

It will be understood that when a feature or element is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached", "fastened", or "coupled" to another feature or element, it can be directly connected, attached, fastened or coupled to the other feature or element or intervening features or elements may be present. In contrast, when a feature or element is referred to as being "directly connected", "directly attached", "directly fastened", or "directly coupled" to another feature or element, there are no intervening features or elements present. Although described or shown with respect to one embodiment, the features and elements so described or shown can apply to other embodiments.

The terminology used herein is for the purpose of describing particular embodiments only and is not intended to be limiting. As used herein, the singular forms "a", "an" and "the" are intended to include the plural forms as well (i.e., at least one of whatever the article modifies), unless the context clearly Indicates otherwise.

Spatially relative terms, such as "under", "below", "lower", "over", "upper" and the like, may be used herein for ease of description to describe one element or feature's relationship to another when the apparatus is right side up as shown in the accompanying drawings.

Terms such as "at least one of A and B" should be understood to mean "only A, only B, or both A and B." The same construction should be applied to longer list (e.g., "at least one of A, B, and C"). In contrast, terms such as "at least one A and at least one B" should be understood to require both A and B.

The terms "first", "second", "third," and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure.

The term "consisting essentially of" means that, in addition to the recited elements, what is claimed may also contain other elements (steps, structures, ingredients, components, etc.) that do not adversely affect the operability of what is claimed for its intended purpose as stated in this disclosure. This term excludes such other elements that adversely affect the operability of what is claimed for its intended purpose as stated in this disclosure, even if such other elements might enhance the operability of what is claimed for some other purpose.

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

B. Radiation Shield Assembly

Figure 2:
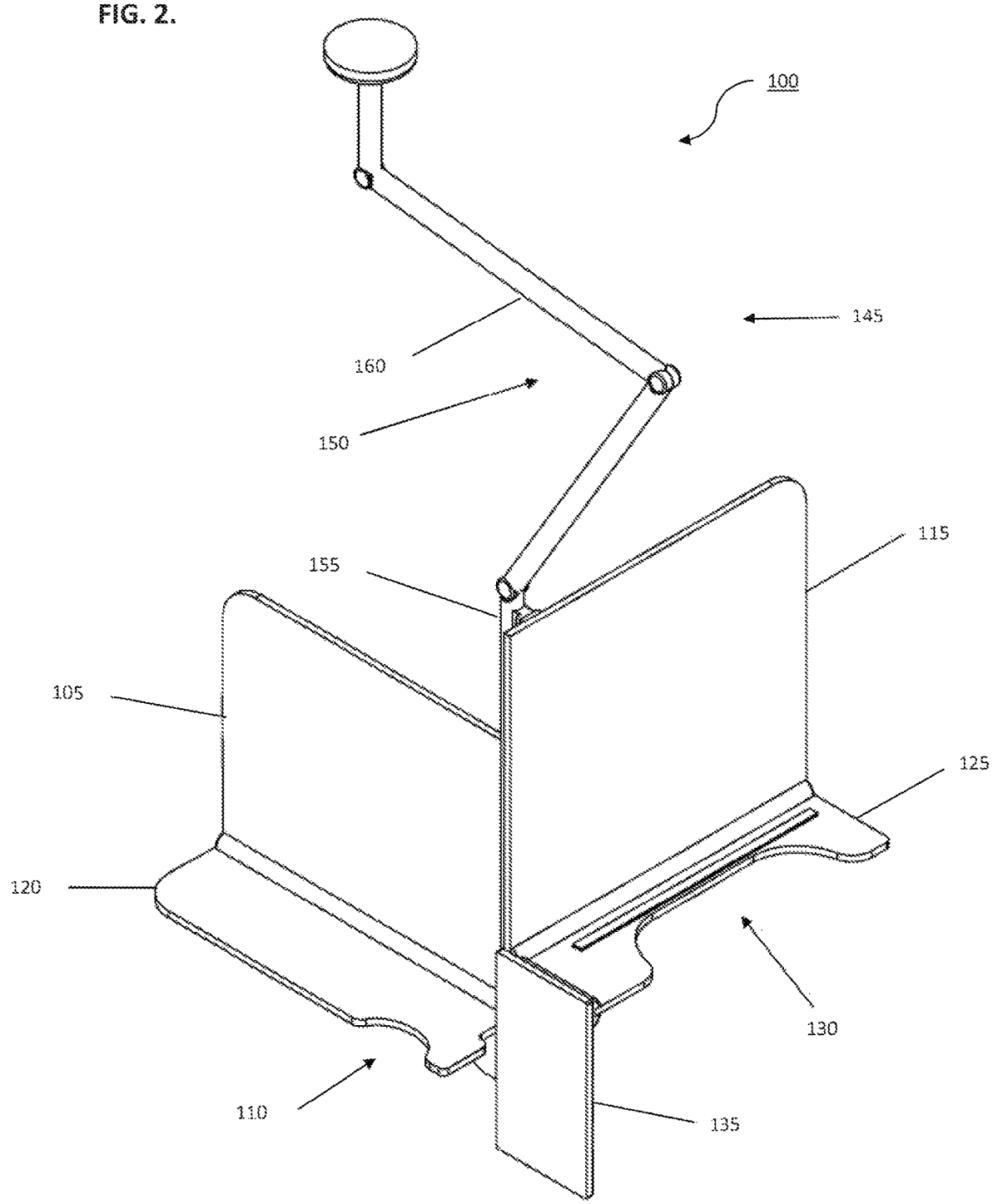
FIG. 2. The shield assembly shown in FIG. 1, in which the first and second vertical shields are orthogonal to one another, in which the second vertical shield is raised.
Figure 3:
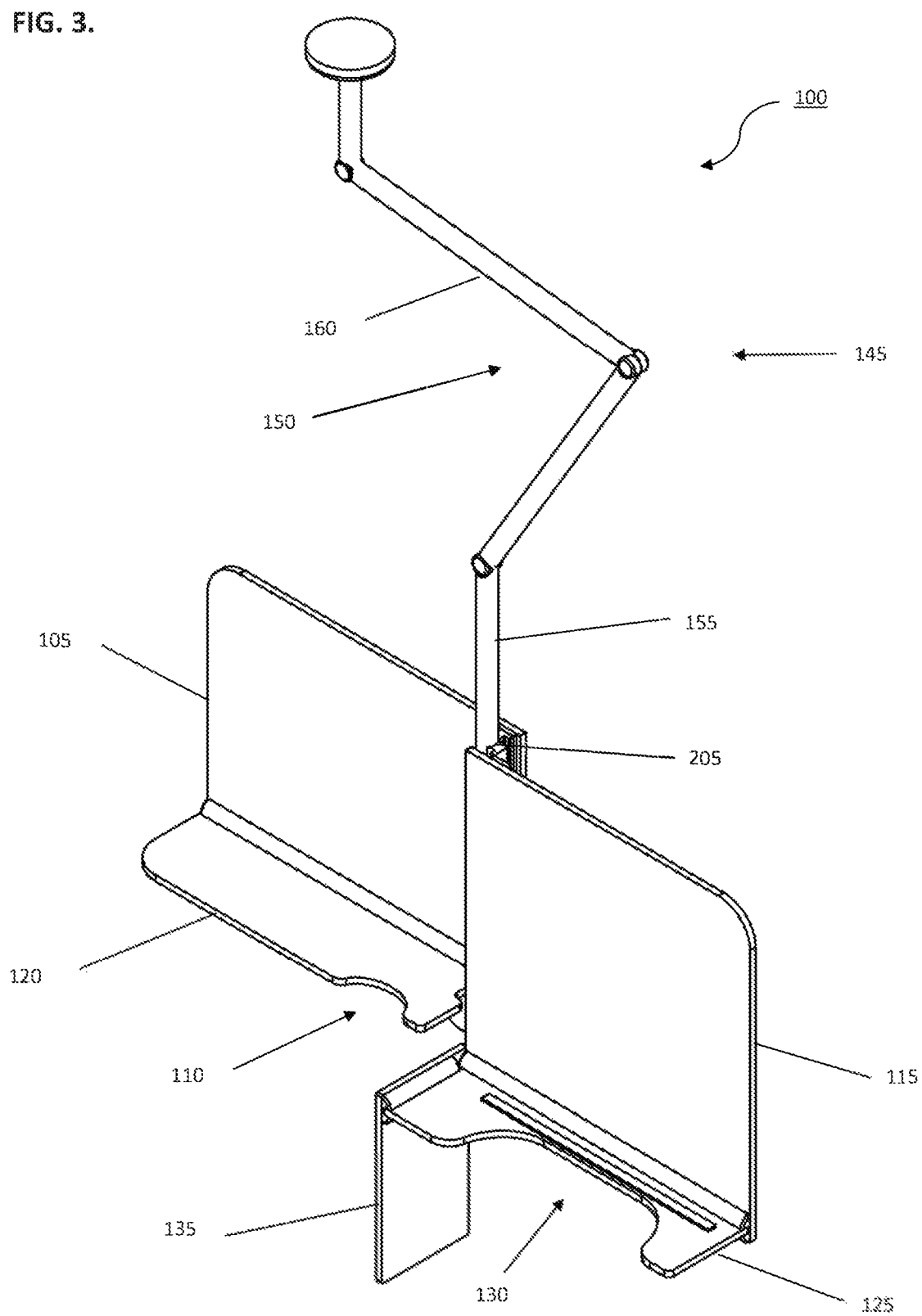
FIG. 3. The shield assembly shown in FIG. 1, in which the second vertical shield has been rotated to be roughly parallel to the first vertical shield.

A radiation shield assembly 100 is provided, configured to block radiation emanating from a radiation source and supported by a support means 145 to support the assembly 100. As shown in FIGS. 1-3, a first shielding means 105 is positioned in a first approximately vertical plane. The first shielding means 105 is fastened to the support means 145, and has an appendage opening 110 dimensioned to allow a human appendage to pass through the first shielding means 105. This gives access to the patient's arm (or alternatively the leg or torso) for the introduction of a medical device (such as an arthroscopic instrument) via the patient's vasculature.

A second shielding means 115 is positioned in a second approximately vertical plane, fastened to the support means 145, to allow the second shielding means 115 to translate and rotate along an approximately vertical axis relative to the first shielding means 105. The second shielding means 115 can thus be raised, lowered, or swung relative to the first shielding means 105 if necessary to gain access to the patient (compare FIGS. 1-3).

To protect the medical staff from radiation shining through the appendage 110, a third shielding means 120 may be positioned to block radiation from the appendage opening 110 in a first approximately horizontal plane that is approximately orthogonal to the first vertical plane. The third shielding means 120 may be fastened to the first shielding means 105 such that the third shielding means 120 translates and rotates with the first shielding means 105. In other words, the first 105 and third shielding means 120 may be static to one another in at least one configuration of the assembly 100 (although in some embodiments they might be mobile in at least one degree of freedom relative to the support arm 150 or other parts of the assembly 100). Additional (or alternative) protection may be provided in the form of a flexible radiopaque member on the bottom of the first shielding means 105. In an alternative embodiment of the shield assembly 100 a flexible radiopaque member 220 is used in place of the third shielding means 120, to intercept radiation emanating through the appendage opening 110. Examples of such flexible radiopaque members 220 include a shroud, a sleeve, a curtain, and one or more leaves of an iris port. They may be constructed from any suitable flexible and radiopaque material.

A fourth shielding means 125 may be positioned in a second approximately horizontal plane. The second horizontal plane is approximately orthogonal to the second vertical plane. The fourth shielding means 125 is fastened to the second shielding means 115 such that the fourth shielding means 125 translates and rotates with the second shielding means 115, for example along the support means 145. Additional protection may be provided in the form of a flexible radiopaque shroud on the bottom of the fourth shielding means 125. In an alternative embodiment of the shield assembly 100 a flexible radiopaque shroud is used in place of the fourth shielding means 125.

A fifth shielding means 135 may be present, positioned in a third approximately vertical plane that is approximately orthogonal to the second approximately vertical plane and to the second approximately horizontal plane, connected to the second shielding means 115 such that the fifth shielding means 135 translates and rotates with the second shielding means 115, and extending downward.

Some embodiments of the shield assembly 100 include a sixth shielding means 140, positioned in a fourth approximately vertical plane, connected to the first shielding means 105 such that the sixth shielding means 140 extends downward. The fourth approximately vertical plane may be approximately parallel to the first vertical plane. The sixth shielding means 140 may be positioned to protect the user's lower body from radiation. The sixth shielding means 140 may take any of numerous suitable forms, including one or more of a generally planar shield, a flexible drape, and an extension of the first shielding means 105.

The first 105 and second shielding means 115 may be configured to swing about a common axis, like a hinge (compare FIGS. 1 and 2). The axis may be the longitudinal axis of the support means 145, for example. In other embodiments, the first 105 and second shielding means 115 may each swing about each of two separate axes, in which said axes are approximately parallel to each other. In some such embodiments, the axes may both be approximately parallel to the longitudinal axis of the support means 145. By analogy, the first 105 and second shielding means 115 are enabled to swing relative to each other like the back and front covers of a book. In some embodiments the first 105 and second 115 shields are capable of assuming relative positions of about 180° from one another, such that they are approximately parallel and/or collinear when seen from above. Such an "open" configuration is useful to form a barrier along the entire length of a prostrate patient. In some embodiments the first 105 and second 115 shields are capable of assuming relative positions at or approaching 0° from one another, in which case they may be in contact with one another, or in close proximity and approximately parallel. In some embodiments the first 105 and the second shielding means 115 are configured to rotate relative to one another over an arc of at least about 90°. In some further embodiments, the first 105 and the second shielding means 115 are configured to rotate relative to one another over an arc of up to about 180°, and in further specific embodiments over an arc of from about 0-180°.

The first 105 and second shielding means 115 may also be configured to translate relative to one another, or to translate together along the support means 145 (compare FIGS. 1 and 2). The shield assembly 100 may comprise a means for translating 225 at least one of the first 105 and second shielding means 115 along the support means 145. By way of example, such means for translating 225 could be an assist mechanism, a counterweight mechanism, an electric motor, a hydraulic mechanism, a pneumatic mechanism, a manual mechanism, or any combination of the foregoing.

The support means 145 may be configured to allow the entire shielding assembly 100 to translate within the operating room, relative to an operating table 305. For example, the support means 145 could be configured to allow manual translation of the entire shielding assembly 100, or to allow mechanical translation of the entire shielding assembly 100 by means of one or more actuators. Some embodiments of the support means 145 constitute a support arm 150. The support arm 150 will be configured to support most of the weight of the assembly 100 (if not all of it). In the illustrated embodiment in FIGS. 2 and 3 the support arm 150 is an elongate steel structure, with a longitudinal axis that is generally vertical when the shield assembly 100 is in use. The support arm 150 can be constructed of any material of sufficient mechanical strength to support the assembly 100, and could be designed by one of ordinary skill in the art. Preferably the support arm 150 is constructed from material that is also radiopaque to the expected frequency and intensity of radiation. For example, some embodiments of the support arm 150 are opaque to X-rays at energies typical of radiology applications.

The support means 145 will be supported by the ceiling, floor, wall, or another structure. When floor-mounted (as in FIG. 4), it can be suspended by various structures. The support means 145 could be Integrally mounted on the floor, or alternatively supported by a stand, either mobile or static.

Figure 5:
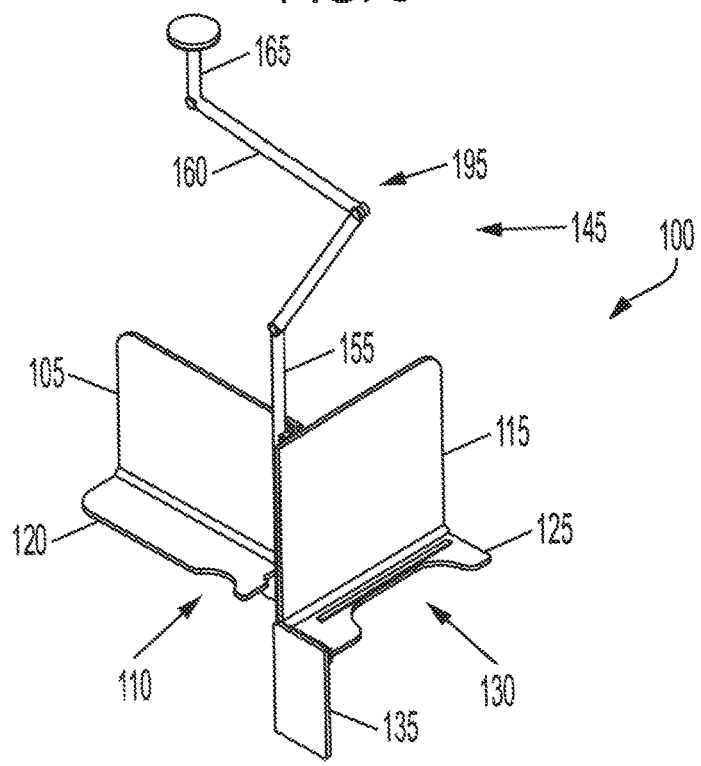
FIG. 5. An embodiment of the shield assembly supported by a ceiling-mounted boom.
Figure 6:
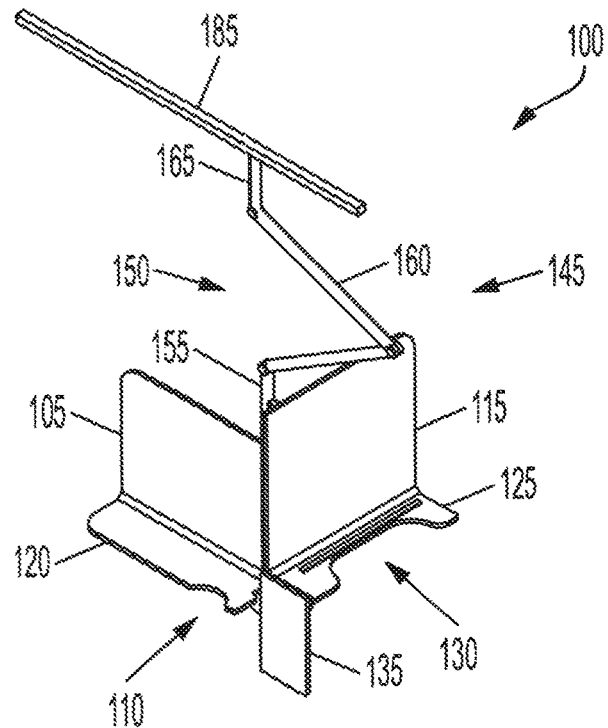
FIG. 6. An embodiment of the shield assembly supported by a ceiling-mounted monorail.
Figure 7:
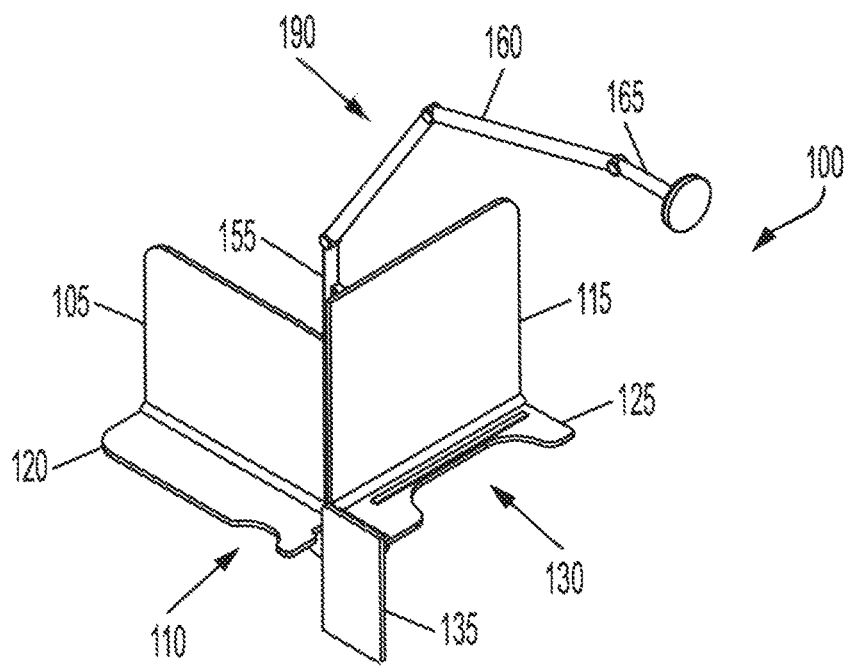
FIG. 7. An embodiment of the shield assembly supported by a wall-mounted boom (wall is invisible).
Figure 8:
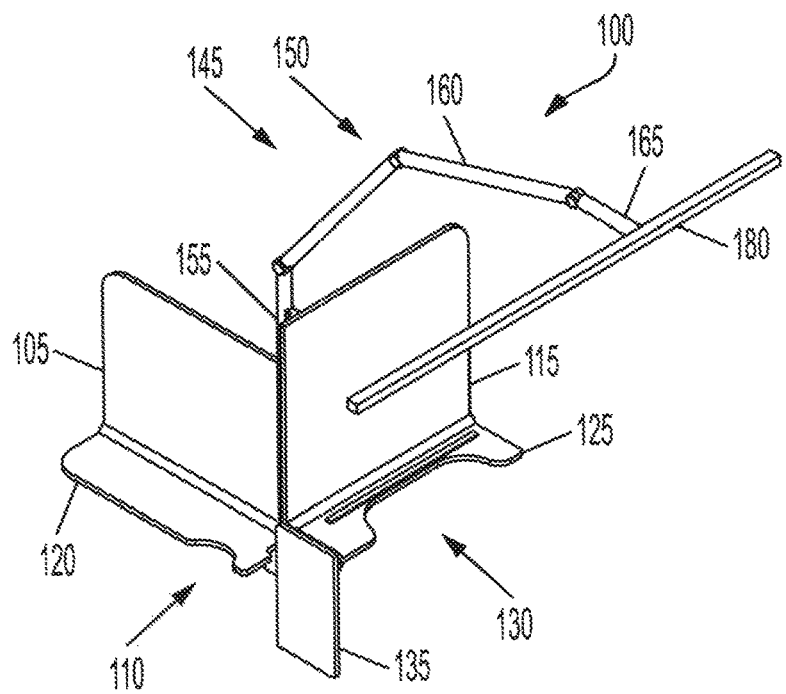
FIG. 8. An embodiment of the shield assembly supported by a supported by a wall-mounted monorail (wall is invisible).
Figure 9:
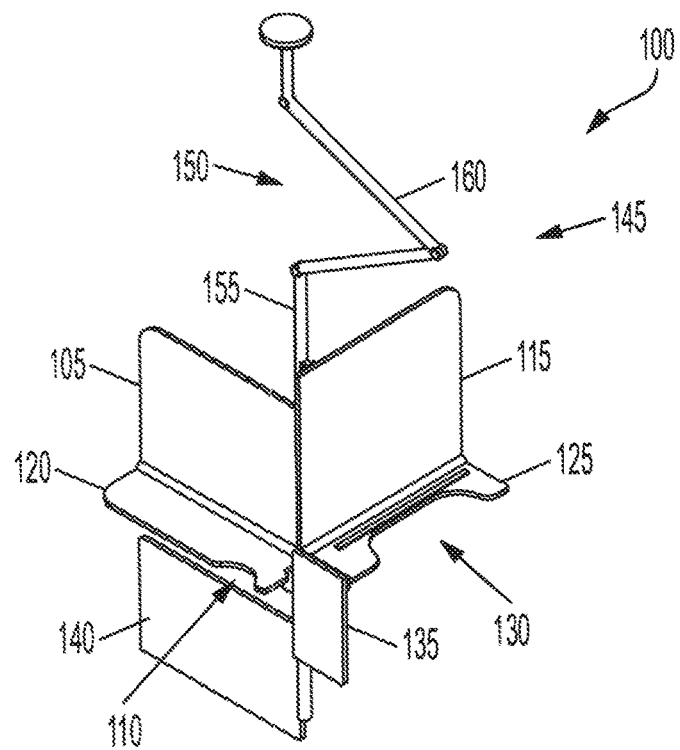
FIG. 9. An embodiment of the shield assembly having a sixth shield.

Some embodiments of the supporting means 145 comprise an approximately vertical mast 155. The supporting means 145 is capable of supporting the shield assembly 100 to some extent. For example, some embodiments of the supporting means 145 are capable of supporting the majority of the weight of the assembly 100. In further embodiments, the supporting means 145 is capable of supporting about the entire weight of the assembly 100, or the entire weight. The mast 155 may be supported by various means. In some embodiments of the radiation shield assembly 100, the mast 155 is supported by a floor stand 170. The floor stand 170 may further comprise a plurality of wheels 175 to allow easy deployment and removal of the assembly 100. In further embodiments of the system, the mast 155 is suspended by an overhead boom 160 (see FIGS. 5 and 7). The use of an overhead boom 160 can provide easy mobility to even a relatively massive assembly 100, allowing the assembly 100 to be emplaced and removed relative to the patient quickly and easily. Various configurations utilizing the boom 160 are contemplated. For example, the mast 155 may be configured to rotate about the longitudinal axis of the overhead boom 160, or to pivot relative to the overhead boom 160. The mast 155 may be capable of translating along the longitudinal axis of the overhead boom 160. In further embodiments of the system, the overhead boom 160 is supported by a second mast 165. The second mast 165 may in turn be supported on a wheeled floor stand 170, mounted on the ceiling, or mounted on a wall. For example, the second mast 165 may be supported by a wall-mounted rail 180 or ceiling-mounted rail 185 (see FIGS. 6 and 8); in such embodiments the second mast 165 may be capable of translating along the wall-mounted rail 180 or ceiling-mounted rail 185. As another example, the second mast 165 may be supported by a wall-mounted swinging arm 190 or ceiling-mounted swinging arm 195 (see FIGS. 5 and 7). In a further embodiment, the second mast 165 may be supported by a swinging arm that is in turn supported by a wall-mounted rail 180 or ceiling-mounted rail 185, and wherein the swinging arm is capable of translating along the wall-mounted rail 180 or ceiling-mounted rail 185.

In some embodiments in which the third horizontal shielding means 120 is present, the first shielding means 105 and the third shielding means 120 are configured to translate together vertically. For example, the first shielding means 105 and the third shielding means 120 may be configured to translate together along the support means 145. The degree of translation may be configured to optimize the shielding of the user from X-rays while the user is standing or sitting. For example, the first shielding means 105 may be configured to translate along such that in a first position a top edge of the first shielding means 105 is at least about the height of an adult human above the floor. Taking into account normal human dimensions, such height could be 175 cm, 180 cm, 185 cm, 190 cm, 195 cm, or 200 cm above the floor.

Similarly, the first shielding means 105 itself will be dimensioned to provide adequate radiation protection when in position during use. For example, it may have a height of at least about the distance from the upper surface of an operating table 305 to an average human's full height. In various embodiments the first shielding means 105 has a height of at least about the distance from the upper surface of an operating table 305 to a height of 175 cm, 180 cm, 185 cm, 190 cm, 195 cm, or 200 cm above the floor when said operating table 305 is on the floor. A greater height has the advantage of shielding a greater area from X-rays, whereas a lesser height has the advantage of reduced weight and cost.

In the illustrated embodiment in the figures, the first shielding means 105 is Intended to be positioned roughly parallel to the long axis of the operating table 305, and protect a user's upper body from X-rays emitted from a point below the table 305. In the illustrated embodiment the first shielding means 105 is a generally planar vertical shield fastened to the support arm 150. Of course, the first shielding means 105 could fulfill its function even if not exactly vertical, and could be designed to be inclined as necessary or desirable to customize the shielded area. Some embodiments of the first vertical shield 105 will be designed to extend above the head of the user, to prevent direct radiation from reaching the user's head. The first vertical shield 105 could be designed to extend above the head of a standing user, or in some circumstances a sitting user. The embodiment of the first vertical shield 105 shown has a length sufficient to extend from the head of the patient to about the waist of the patient. Such a configuration is particularly useful in procedures in which radiography is used to visualize the patient's thoracic region. The length could be increased to provide broader protection, but such Increase in length must be balanced with the additional weight and reduced flexibility in configuration that will accompany such changes.

In the illustrated embodiment an opening 110 is shown in the first shielding means 105 to allow the patient's arm to extend from the shielded area. The opening 110 may optionally contain flexible shielding material such as a radiopaque curtain or flexible flanges 220. The opening 110 as shown is semicircular, but may take any shape that allows the patient's appendage to extend through the shield. The opening 110 presents a possible path for radiation leaks. The third shielding means 120 is positioned to block radiation shining through the opening 110 from irradiating the user. In the illustrated embodiment, the third shielding means 120 is a horizontal shield positioned over the opening 110 and orthogonal to the first vertical shield 105. This particular configuration is useful to block radiation from an emitted position below the opening 110 and on the side of the vertical shield opposite to where the user is standing. The third shielding means 120 can be oriented differently to accommodate a different emitted position relative to the opening 110.

In the Illustrated embodiment of FIGS. 1-3, the second shielding means 115 is configured to rotate and translate relative to the first shielding means 105 to allow the assembly 100 to be adjusted according to the dimensions of the patient and to allow the assembly 100 to be reconfigured to provide varying degrees of access to the patient and protection from radiation. In the illustrated embodiment it takes the form of a second approximately vertical shield 115 connected to the support arm 150 so as to allow it to rotate about the longitudinal axis of the arm and translate parallel to the same longitudinal axis. In FIG. 1 the second vertical shield 115 is shown in a position orthogonal to the first vertical shield 105. Such a configuration is useful in practice to give the user access to a patient's legs when the second vertical shield 115 crosses the patient's body. It could also be lowered to the table 305 to form a complete shield if the patient is positioned with the head closest to the second vertical shield 115. In FIG. 3 the second vertical shield 115 is shown generally parallel to the first vertical shield 105.

The fourth shielding means 125 functions to block radiation that might shine from under the second shielding means 115 when the second shielding means 115 is positioned above the table 305. In the accompanying figures the fourth shielding means 125 is shown as a horizontal shield with a cutout 130. This trapezoidal cutout 130 functions to provide access to a patient's groin during the procedure, which can be useful to allow access to the femoral vein for arthroscopic Insertion. The cutout 130 is a useful, but optional, feature of the second horizontal shield 125. In the illustrated embodiment the second horizontal shield 125 is positioned to intercept radiation emitted from below an operating table 305, but this structure could be positioned differently to intercept radiation from another direction.

The fifth shielding means 135, when present, functions to intercept radiation from exposing a user's lower body when the user is located on the opposite side of the support arm 150 as the radiation source. Such a structure is not generally necessary below the first shielding means 150 because operating tables typically are equipped with leaded curtains hanging from the operating table for procedures that require radiological monitoring. However, the curtain does not always run the entire length of the table or extend along the width of the table.

Most of the surface area of the shielding means are opaque to the frequencies and intensities of radiation which they are Intended to block. Some embodiments of the shielding means may be entirely radiopaque. Exemplary materials that are radiopaque to X-rays include lead plates, lead filings, leaded acrylic glass, and polymer suspensions of lead particles. Other heavy metals, such as barium, may be used, although lead has the advantage of a very high atomic number and stable nuclides. As thickness increases along the radiation vector radiopacity increases. In designing the shielding means a balance will be struck between achieving adequate radiopacity and limiting the weight of the apparatus. For example, some embodiments of the lead shield will be about 0.5-1.5 mm thick. Further embodiments of the lead shield will be about 0.8-1.0 mm thick. Less dense materials, such as leaded acrylic, must be thicker to achieve the same level of radiopacity as lead. For example, some embodiments of the leaded acrylic shield will be about 12-35 mm thick. Further embodiments of the leaded acrylic shield will be about 18-22 mm thick. Lead barium type glass is another suitable material. For example, some embodiments of the lead barium type glass shield will be about 7-17 mm thick. Further embodiments of the lead barium type glass shield will be about 7, 9, 14, or 17 mm thick. Comparing these exemplary materials, lead has the advantage of better radiopacity per unit thickness, while leaded acrylic and lead barium type glass have the advantage of visual transparency and X-ray opacity. In some embodiments of the assembly 100 at least one of the first through fifth shielding means 105, 115, 120, 125, 135 is transparent to visible light. In such embodiments the transparent shielding means may have an optical transmissivity that equals or exceeds one of 50%, 55%, 60%, 65%, 70%, 75%, 80%, 85%, 90%, 95%, 99%, and 100%.

Outside of the context of any specific material, the radiopacity of the shielding means can be expressed as millimeter-lead equivalents. In various embodiments of the system, at least one of the first 105, second 115, third 120, fourth 125, or fifth shielding means 135 has a radiopacity of least 0.5 mm, 1.0 mm, 1.5, 2, 3, or 3.3 mm lead equivalent.

Any of the shielding means described above may be joined to one another or joined to the support means 145 via a radiopaque joint 205. Such a radiopaque joint 205 will minimize the transmission of radiation from the generator through the joint 205. This can be accomplished between plates for example by joining the plates with a sufficiently narrow gap that a straight line cannot be traced from the radiation source through the gap when in position as intended at the operating table 305. Such joints 205 can be constructed using, for example, radiopaque braces or lap joints. A radiopaque joint 205 with a support arm 150 can be constructed, for example, using a radiopaque sleeve around the support arm 150 fastened to the shielding means.

The radiation shield assembly 100 is supported by the support arm 150 and positioned to locate a first and second shield assembly between the patient and the user. The first shield assembly is fastened to the support arm 150, comprising the first generally vertical shield 105 and the first generally horizontal shield 120. The second shield assembly is also fastened to the support arm 150 so as to rotate and translate along the longitudinal axis of the support arm 150 relative to the first shield assembly. The second shield assembly comprises a second generally planar vertical shield 115 positioned above the table 305; a second generally horizontal shield 125 connected to the second vertical shield 115 and positioned above the table 305; and a lower generally planar vertical shield 135 extending from the second horizontal shield 125 to below the table 305. The second vertical shield 115 may be rotated about its axis to be approximately orthogonal to the longitudinal axis of the table 305 or to be approximately parallel to the longitudinal axis of the table 305.

The shield assembly may further comprise one or more sterile coverings to maintain asepsis during procedures. Such coverings may be constructed from any material that is amenable to sterilization. The coverings may also be constructed from material that is sterile when manufactured, even if such material is not amenable to subsequent sterilization; such embodiments of the coverings may be considered to be disposable. The material that is amenable to sterilization may be amenable to only a single method of sterilization, or to multiple methods. Known methods of sterilization include chemical sterilization, heat sterilization (both wet and dry), and sterilization by radiation (such as gamma). The coverings may be constructed from transparent material, which has the advantage of allowing medical staff to view the patient if one or more of the shields is also transparent. One or more of the coverings may be radiolucent, as their primary function is to provide an aseptic environment, not to provide additional radiation protection per se. In some embodiments of the system all of the coverings are radiolucent.

Figure 19:
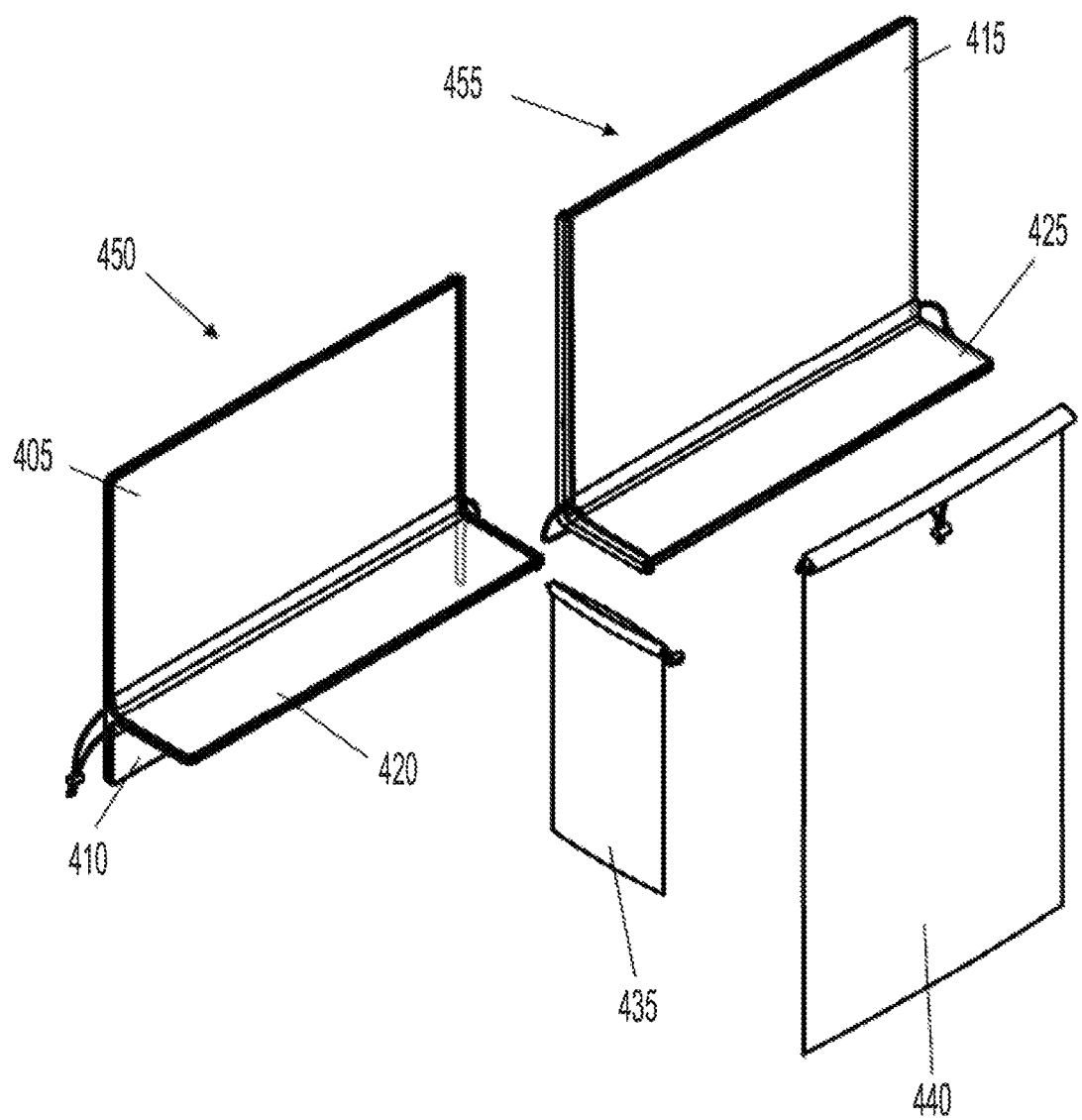
FIG. 19. Embodiments of sterile coverings for use with certain embodiments of the shield assembly.

The shield assembly may comprise one or more of: a first covering 405 on the first shielding means or first vertical shield; a second covering 415 on the second shielding means or second vertical shield; a third covering 420 on the third shielding means or first horizontal shield; a fourth covering 425 on the fourth shielding means or second horizontal shield; a fifth covering 435 on the fifth shielding means or lower vertical shield; a sixth covering 410 on the sixth shielding means or third generally vertical shield; and a seventh covering 440 on the supporting means or the mast. In some embodiments of the shield assembly, the first, third, and sixth coverings 405, 420, 410 are parts of a single component. In some embodiments of the shield assembly, the second and fourth coverings 415, 425 are parts of a single component. In the embodiment shown in FIG. 19 a first cover unit 450 comprises the first, third, and sixth coverings 405, 420, 410 that surround the components of the first shield assembly; and second cover unit 455 comprises the second and fourth coverings 415, 425 that surround the components of the second shield assembly.

The sterile covering may take various shapes. Examples Include a drape that hangs down from a rod or other support structure positioned above the drape. Another example is an encasement that covers multiple sides of one or more of the shields. Such an encasement may be hard-walled (like a box) or soft (like a bag). A soft encasement may include means to tighten the covering over the shield, such as a draw string. The covering may be shaped to accommodate one or more of the shields.

Figure 18:
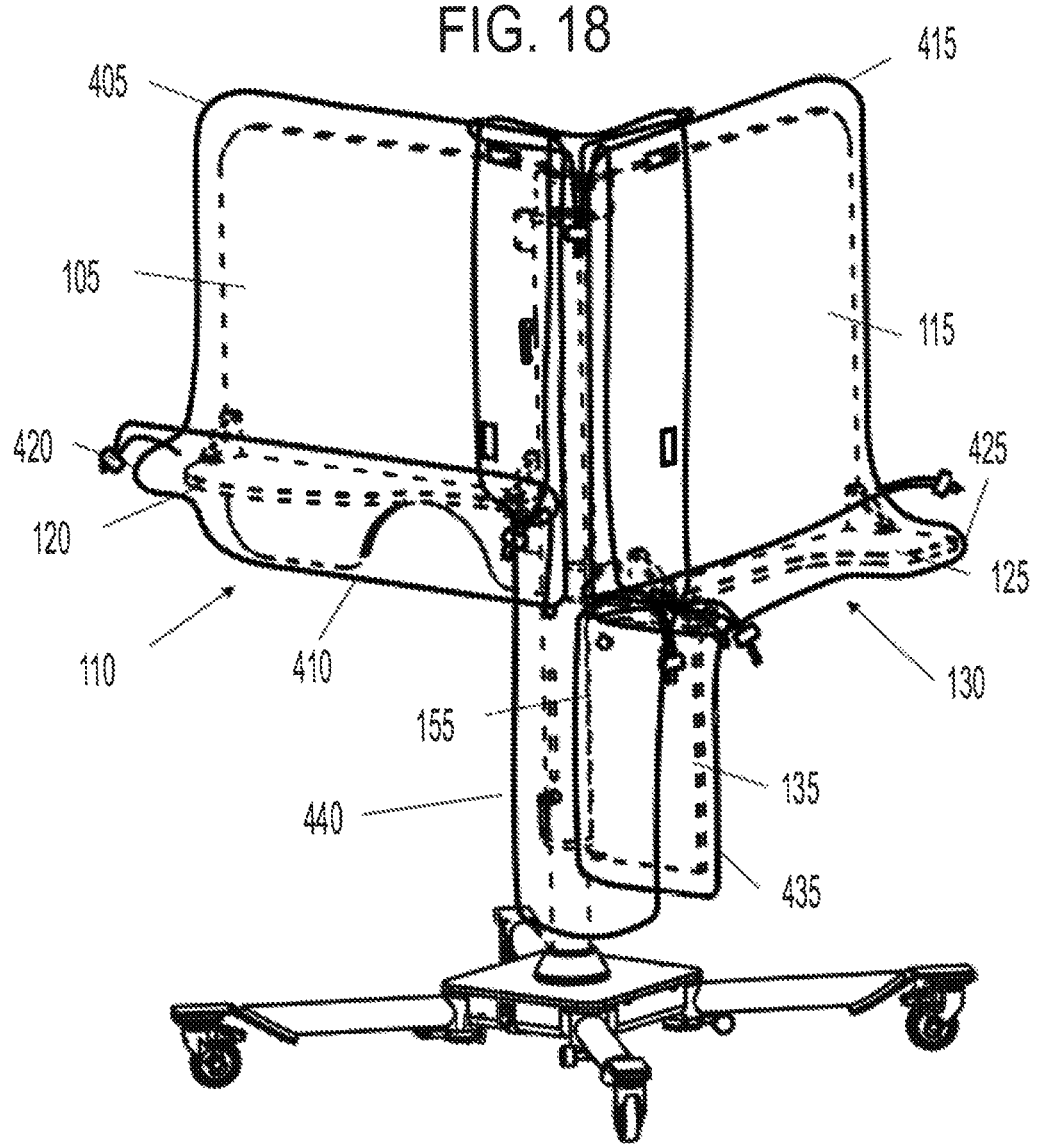
FIG. 18. An embodiment of the shield assembly with sterile coverings in place.

FIG. 18 shows an embodiment of the shield assembly with sterile coverings in place. The first shield assembly (including the first vertical shield and first horizontal shield) is covered by a soft cover unit made of transparent plastic. The soft cover unit Includes a first covering section 405 that fits over the first vertical shield and a third covering section 420 that fits over the first horizontal shield. The soft cover unit over the first shield assembly can be tightened in place using a draw string. The second shield assembly is partially covered by a second soft cover unit; the second soft cover unit includes a second covering 415 surrounding the second vertical shield and a fourth covering 425 over the second horizontal shield. The lower vertical shield is covered by a fifth covering 435, which takes the form of a hanging drape. The support mast is also covered by a seventh covering 440, such as a sterilizable drape. Note the small adhesive patches by which the support mast drape is adhered to the soft covers of the first and second shield assemblies.

Figure 10:
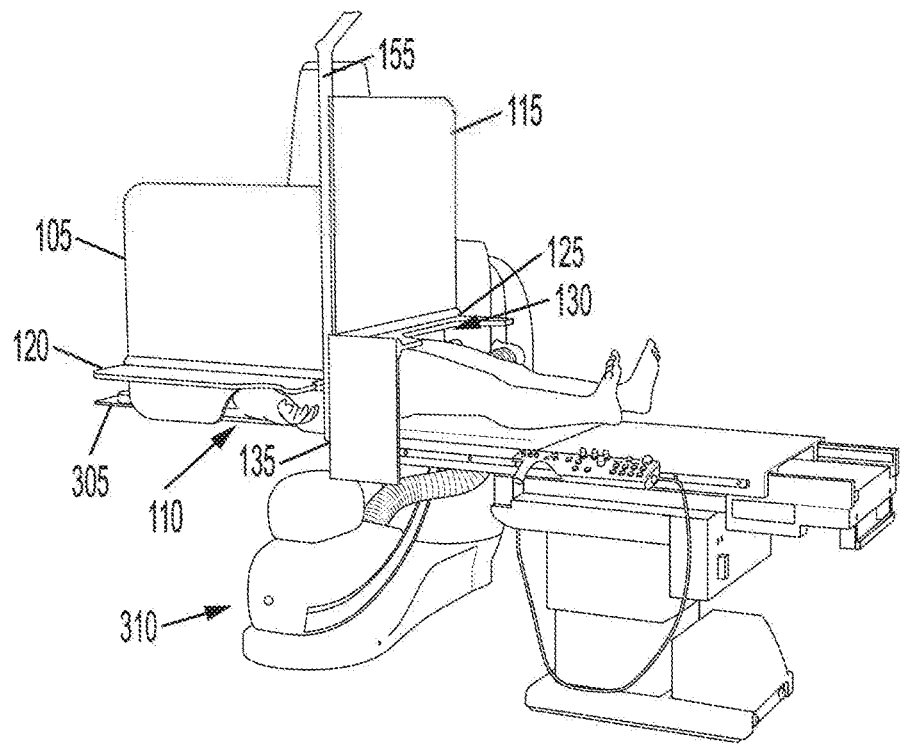
FIG. 10. A perspective view of an embodiment of the shielding system including an operating table, X-ray generator, and X-ray image intensifier. A patient is shown in an exemplary position.
Figure 11:
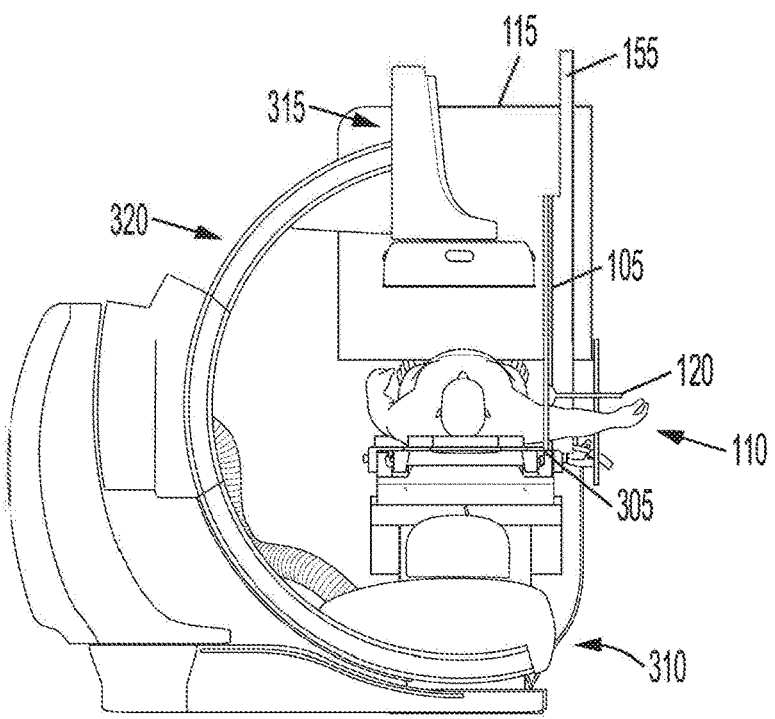
FIG. 11. A front view of the embodiment of the shielding system in FIG. 10.

The shielding assembly may be part of a greater system comprising an operating table 305, X-ray generator 310, and image Intensifier 315 (see FIGS. 10 and 11). The X-ray generator 310 will be positioned to direct X-rays through the table 305 and to the image intensifier 315 on the other side, as is known in the art. The generator 310 and image intensifier 315 may be mutually mounted on a C-arm 320, for example. The operating table 305 will frequently have a radiopaque curtain 325 hanging from at least one side of the table 305. The curtain 325 may also extend around two or more sides of the table 305. The curtain 325 is particularly useful when the system is configured with the X-ray generator 310 below the table 305. The patient will generally be "prostrate," meaning that the patient patent is lying on the table 305 in any suitable orientation, including supine, prone, and lying on the side. Conventionally the patient will be positioned on a table 305, between an X-ray generator 310 and an image intensifier 315, for example as commonly mounted on a C-arm 320. In the accompanying Illustrations the X-ray generator 310 is shown below the patient, which is one commonly used configuration, but not the only configuration in which the system could be used. The table (such as an operating table 305) is capable of supporting the patient. Depending on the age and size of the patient, various configurations of operating table 305 could be used. The image intensifier 315 will be positioned to receive X-rays projected from the X-ray generator 310 (such as being positioned above the table 305 if the X-ray generator 310 is below). Typically a radiopaque curtain shield 325 extends downwardly from the table 305 on the side one which medical personnel will be working (the "first side"). The first shielding means 105 may be positioned to contact the table's edge along its long dimension, or such that the bottom edge to the first shielding means 105 is below the surface of the table 305 along its long dimension. The second shielding means 115 may also be positioned parallel to the long dimension of the table 305, so as to form a barrier between the user and the patient's lower extremities. In such a configuration the second shielding means 115 will also be positioned so that its lower edge either contacts the table 305 or hangs below the elevation of the table's surface so as to block radiation from reaching the user. Alternatively, the second shielding means 115 may be rotated relative to the first shielding means 105 at an approximately orthogonal angle, so as to cross the operating table 305 laterally. If the second shielding means 115 has a cutout at the bottom to accommodate the patient's body, this can provide the user access to the patient's lower extremities, for example to gain access to the femoral vein. The second shielding means 115 can be elevated along the support means 145 appropriately to accommodate the patient's physiology. It is also contemplated that the second shielding means 115 could be positioned laterally across the table 305, and in contact with the table 305, for example if the patient's head is located proximate to the second shielding means 115 (not shown). Thus a medical device, such as a catheter or an arthroscopy Instrument, can be Inserted into the patient's vasculature through an arm or leg extending past the first 105 or second shielding means 115 while minimizing the radiation that reaches the user.

A method of radiology is provided, using any embodiment of the radiation shield assembly 100 disclosed above. The method comprises positioning any one of the radiation shield assemblies or systems above between a patient and a user, such that an appendage of the patient extends through an appendage opening 110 in the shield assembly; inserting a medical device into vasculature of the appendage; and Irradiating the patient using a radiation generator 310 positioned such that radiation passes at least partially through the patient while being blocked from reaching the user by the shield assembly 100.

C. Example

Analysis was performed at the testing location for the purpose of the evaluation of an embodiment of the shielding system. Secondary scattered radiation was created with two CIRS 76-125 patient equivalent phantoms using a Siemens C-ARM X-ray source that was normally used for fluoroscopy operations. Analysis was performed to survey scattered radiation through custom shielding and compared against no protective shielding versus lead apron results.

Figure 4:
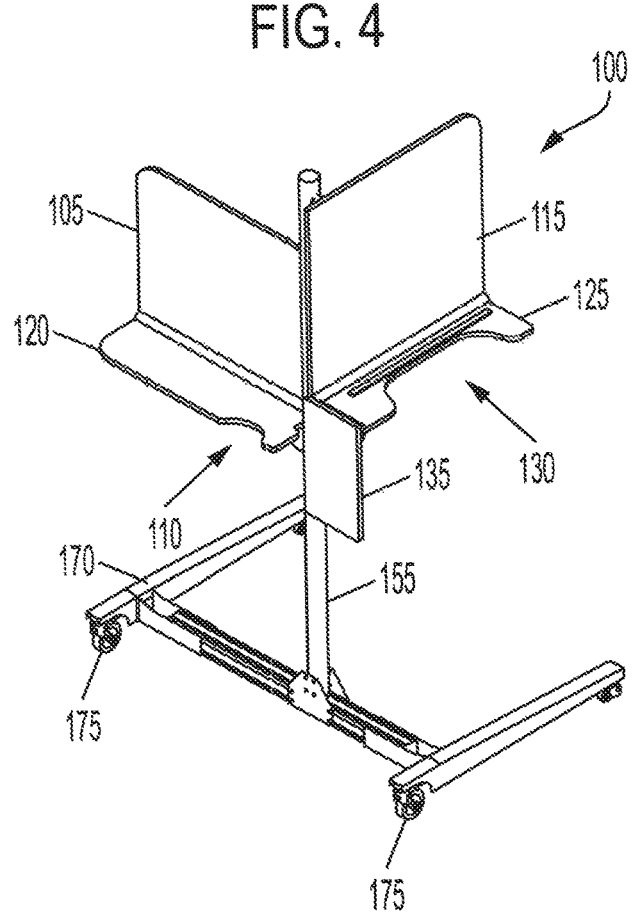
FIG. 4. An embodiment of the shield assembly supported by a floor unit.

The test sample was a custom lead-acrylic radiation protective shield fabricated specifically for C-ARM applications. The shielding consists of a series of custom fabricated, 18.8 mm thick lead-acrylic material (Sharp Mfg. West Bridgewater, MA), having a minimum density of 4.36 g cm$^{-3}$, a refractive index of 1.71, a thermal expansion coefficient of 8E-6/° C. (30-380°), and a Knoop hardness of 370. Specifically, the material is lead barium type glass of high optical grade with greater than 60 percent heavy metal oxide, at least 55 percent PbO. The lead equivalency of this material is guaranteed by the manufacture to be greater than 3.3 mm Pb. The custom fabricated shielding design with labels was constructed generally as shown in FIG. 4. With the exception of the support system which is made from aluminum, the shielding system is entirely made from the exact same source material. All the panels were fabricated and cut by the manufacturer.

Scattered radiation was created using a Siemens Model 10394668 with Serial No 1398 Medical C-ARM source through the CIRS 76-125 Lead-Acrylic Patient Equivalent Phantom extremity and torso used to represent a patient torso with an arm (Computerized Imaging Reference Systems, Inc., Norfolk, VA). The Siemens Medical C-ARM has a reported Inherent filtration of 0.8 mm Al at 70 kV along with the diameter chamber, size B with 0.2 mm Al at 70 kV. No secondary filtration was used for the measurements discussed in this report.

Radiation measurements were made using a Victoreen 470A Panoramic Survey Meter with Serial No 2079. Calibration was performed using a Cs-137 isotope source at the University of Alabama at Birmingham (UAB) Radiology Labs.

Comparisons with lead aprons were carried out using two products, a Techno Aide lead apron with serial no T116969, and a Xenolite with serial no 1 02 001. According to the manufactures' information, both lead aprons have a lead equivalency of 0.5 mm Pb.

Test methods and procedures were guided by ASTM F3094 (ASTM International "Standard Test Method for Determining Protection Provided by X-ray Shielding Garments Used in Medical X-ray Fluoroscopy from Sources of Scattered X-Rays" *ASTM Volume* 11.03 *Occupational Health and Safety; Protective Clothing* (2017)), IEC 61331-1 (International Electrotechnical Commission, "Protective devices against diagnostic medical X-radiation—Part 1: Determination of attenuation properties of materials" (2014) available at https://webstore.iec.ch/publication/ 5289), and a medical physicist. A testing methodology was developed and created prior to being performed. ASTM F3094 and IEC 61331-1 are incorporated herein by reference so as to enable a person of ordinary skill in the art to perform the protocols.

The custom fabricated lead-acrylic shielding was tested for the attenuation of scattered radiation as well as uniformity. In addition, measurements were made along the major edges of the total shield as well as a semi-circular section where the physician will place the patient's arm during procedure. Equivalent scattered radiation measurements were compared against 0.5 mm lead equivalent lead aprons. The final set of measurements were made with no shielding in place. All data was recorded on site. All measurements were recorded using a 10 second exposure time and repeated at a minimal of three times. The criteria of protection rating was based on the measured, scattered radiation attenuation from an 81 kV X-ray C-ARM source.

Radiation detected by the Victoreen 470A represents scattered X-ray radiation created by the Interaction of X-rays with the CIRS 76-125 patient equivalent phantom. The distance between the C-ARM X-ray source was set at the default distance used for patient examinations of 17 inches or 43.18 cm. This protocol is referred to herein as the "Modified ASTM F3094/IEC 61331-1 Protocol."

Average scattered radiation measurements made with no shielding can be found in Table 1 below. All measurements were made in triplicate at a minimal. Radiation measurements were first made with the custom, fabricated shielding in place so that the exact position of the shield, phantom, and detector could be marked for subsequent measurements without any shielding or comparison measurements with the two lead aprons.

TABLE 1

Summary of Phantom, Scattered Exposure without Protective Shielding

| Measurement Region | mR/hr Avg (Std Dev) |
|---|---|
| Centered | 3.725 (0.095) |
| Bottom, Edge | 1.65 (0.1) |
| Right, Edge | 1.67 (0.057) |
| Top, Edge | 2.7 (0.0) |
| Left, Edge | 3.55 (0.057) |
| Bottom, Left, Edge | 2.267 (0.058) |

Figure 12:
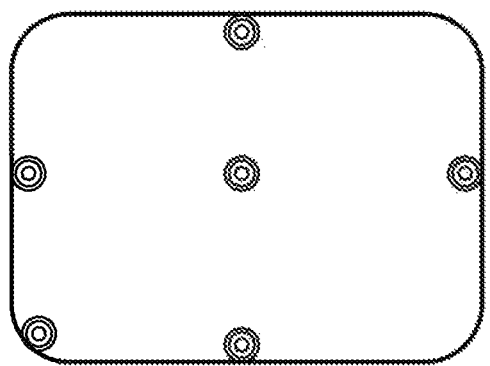
FIG. 12. Illustration of sensor positioning on an exemplary shield during dosimetry testing.

All measurements were made in triplicate at a minimal. Average scattered radiation measurements made with the custom, fabricated lead-acrylic shield (FIG. 12) can be found in Table 2 below. Measurements made through the custom fabricated shielding as well as currently accepted lead aprons are very low intensity and only slightly above background radiation. As a result, replicate measurements yielded a low standard deviation as compared to measurements without any shielding in Table 1 above.

TABLE 2

Summary of Phantom, Scattered Exposure with Custom Fabricated Shielding

| Measurement Region | mR/hr (Std Dev) |
|---|---|
| Centered | 0.083 (0.029) |
| Bottom, Edge | 0.15 (0.0) |
| Right, Edge | 0.15 (0.0) |
| Top, Edge | 0.15 (0.077) |
| Left, Edge | 0.2 (0.0) |
| Bottom, Left, Edge | 0.25 (0.0) |

In addition, measurements were performed to detect the levels of radiation in the precise position of the physician while in use. Measurements were specifically made at the physicians groin height as well as the physician's chest height. The results are summarized below in Table 3.

TABLE 3

Summary of Phantom, Scattered Exposure with Custom Fabricated Shielding

| Measurement Region | mR/hr (Std Dev) |
|---|---|
| Physician Mid-Chest | 0.0773 (0.0343) |
| Physician Groin | 0.21 (0.022) |

Figure 13:
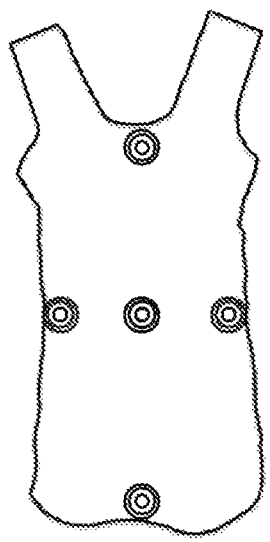
FIG. 13. Illustration of sensor positioning on a lead apron during dosimetry testing.

Scattered radiation measurements were then made with a Techno Aide 0.5 mm lead equivalent apron and can be found in Table 4 below. Measurements were made through a lead apron (FIG. 13) for the purpose of comparing an accepted, medical radiation protective device to the one being proposed in this study. Strict comparison under actual, real-life positions was used in an attempt to provide the most accurate information and comparison. A graphical representation has been created below with Table 4 summarizing the observed averages for scattered radiation measurements with standard deviations.

TABLE 4

Summary of Phantom, Scattered Exposure with Techno Aide 0.5 mmPb Lead Apron

| Measurement Region | mR/hr (Std Dev) |
|---|---|
| Centered | 0.075 (0.027) |
| Bottom, Edge | 0.075 (0.029) |
| Right, Edge | 0.1125 (0.025) |
| Top, Edge | 0.1 (0.0) |
| Left, Edge | 0.1 (0.0) |

Once survey measurements had been completed on the first 0.5 mm lead equivalent apron, a second lead apron was selected and replicate measurements were performed exactly as done for the Techno Aide product. The measurements for average for scattered radiation measurements are summarized below in Table 5 for the second, XenoLite lead apron comparison.

TABLE 5

Summary of Phantom, Scattered Exposure with XenoLite 0.5 mmPb Lead Apron

| Measurement Region | Avg (Std Dev), mR/hr |
|---|---|
| Centered | 0.05 (0.0) |
| Bottom, Edge | 0.1 (0.0) |
| Right, Edge | 0.05 (0.0) |
| Top, Edge | 0.1 (0.0) |
| Left, Edge | 0.067 (0.03) |

Two shield components were measured as a representative for uniformity to ensure that no voids are present in the overall shield apparatus. These measurements were performed in the same manner as described above. The results can be found in FIGS. 14 and 15. The data is represented in the same format as in Tables 1-4 with the reported average scattered radiation measurement values and standard deviation in parentheses.

Figure 14:
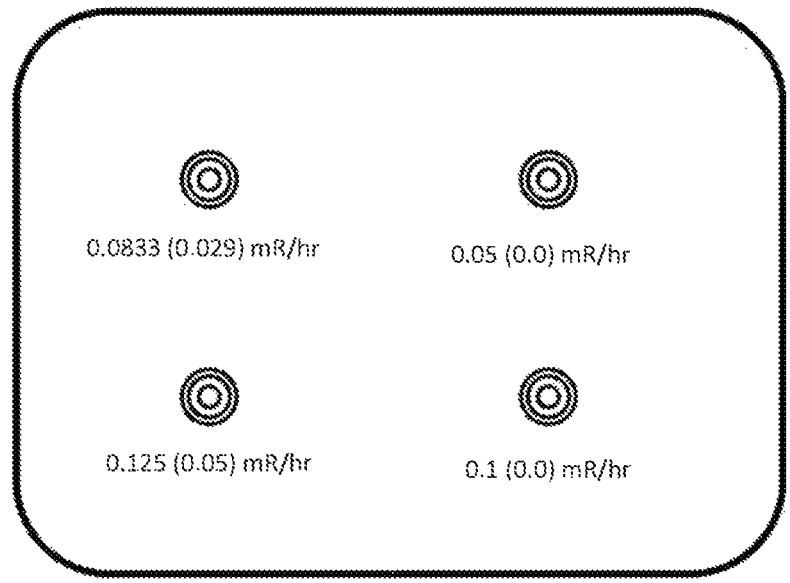
FIG. 14. Illustration of sensor positioning on shield during uniformity testing.

As demonstrated by FIG. 14, no significant voids were observed while performing survey measurements of Main Panel A. Radiation measurements yielded values very similar to previous measurements previously reported from centering on Individual panels. An additional note, replicate measurements were essentially identical and yielding a low standard deviation.

Figure 15:
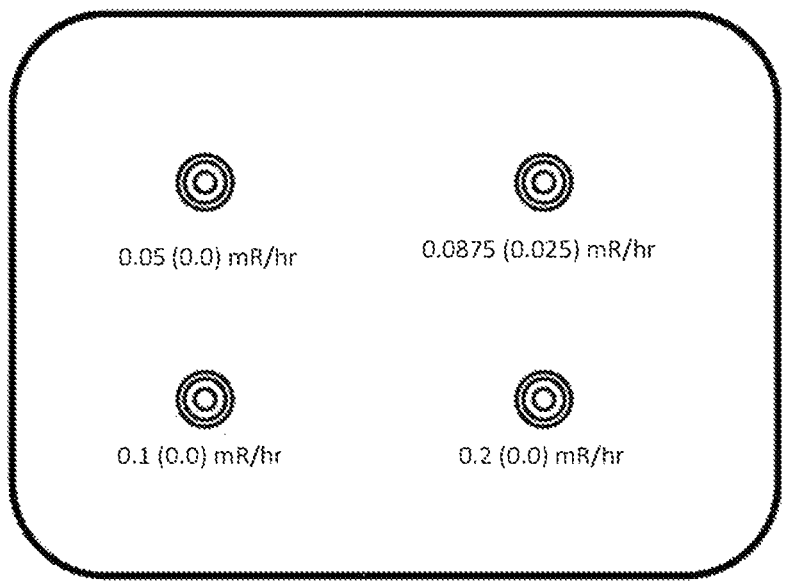
FIG. 15. Illustration of sensor results on shield in uniformity testing.
Figure 16:
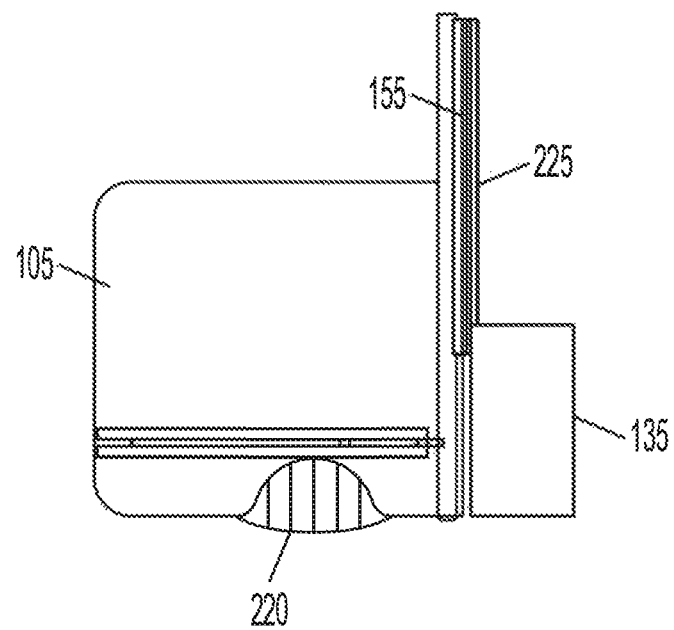
FIG. 16. An embodiment of the shield assembly comprising a flexible radiopaque member on the bottom of the first shielding means, and showing a pneumatic piston for raising and lowering the second horizontal shield.
Figure 17:
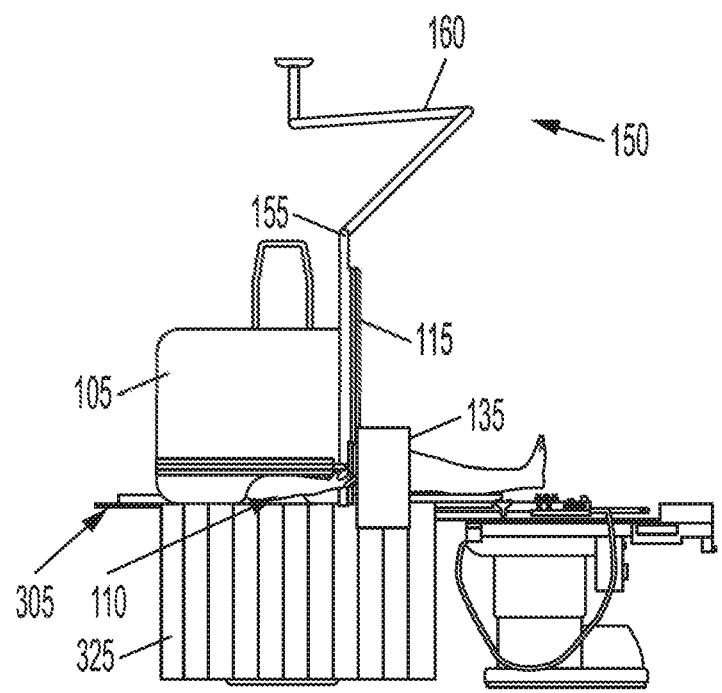
FIG. 17. An embodiment of the shielding system including an operating table, X-ray generator, and X-ray Image intensifier showing a radiopaque drape below the operating table.

As demonstrated by FIG. 15, the four regions were surveyed for uniformity with Main Body Panel A. The average measured radiation value is represented above with the standard deviation in parenthesis. A quick comparison between FIGS. 14 and 15 show very similar values between Main Panel A and Main Body Panel A.

Pass/fail criteria is based on the pre-accepted performance criteria of industrial grade lead-acrylic custom fabricated into a C-ARM shielding apparatus. In addition, this shielding apparatus must provide protection equal to or greater than currently, accepted lead aprons used for the same application. Using the state of Alabama guide that a medical worker receives no more than 5 Rem per year as a shallow dose equivalent and used as the pass/fail criteria.

This study endpoints are based on the successful completion of all measurements dictated by Alabama State guidelines for protective devices used by physicians in C-ARM patient examinations. The study endpoint is specifically based on comparable measurements made using currently accepted lead aprons against no protective shielding of any kind versus the custom fabricated lead-acrylic shielding.

The levels of radiation detectable behind the sponsoring custom, fabricated lead-acrylic shielding were consistent with calculated values based on the manufacture's performance criteria. The levels of radiation detected are within the maximum allowable permitted dose of radiation for medical workers.

When compared to currently accepted lead aprons, relatively equal levels of attenuated radiation were detected behind the custom shielding. The performance of the custom shielding and lead aprons is due in large part to the detection of secondary radiation in this case, as opposed to primary radiation. Scatter equivalent primary radiation is used to determine the official lead equivalency of a material. Under actual scatter conditions such as those used in this study, the measurable amount of secondary radiation is so low that one would not expect measurable differences between materials with different lead equivalency.

Using the currently accepted dose equivalent of 5 rems (R) per year, 52 work-weeks a year, and 40-hours of exposure a week, total annual exposure with this shielding prototype was calculated. According to the highest observed radiation measurements made during this study of 0.25 mR/hr, a 40-hour work week would yield a total dose of 10 mR per week. Using the average value calculated from all measurements of 0.164 mR/hr, a 40-hour work-week would yield a total dose of 6.6 mR per week. Using the maximum possible dose of 10 mR per week, the custom fabricated shielding apparatus would yield a total dose of 520 mR or 0.52 R annual.

D. Conclusion

The foregoing description Illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further Intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not Intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

The following is claimed:

1. A radiation shield assembly, configured to block radiation emanating from a radiation source from below a table for supporting a patient, the assembly comprising:
    (a) a support arm constructed to support at least the majority of the weight of the shield assembly;
    (b) a first generally planar vertical shield; and
    (c) a second generally planar vertical shield;
    (d) at least one of: (i) a first sterile covering on the first generally planar vertical shield; and (ii) a second sterile covering on the second generally planar vertical shield;
    wherein the first generally planar vertical shield is joined to the second generally planar vertical shield to form a radiopaque barrier;
    wherein the radiation shield assembly is configured to allow at least one of the first generally planar vertical shield and the second generally planar vertical shield to be rotated relative to the other about an approximately vertical axis; and
    wherein the radiation shield assembly is configured to position the first generally planar vertical shield and the second generally planar vertical shield to protect a user's upper body from radiation emanating from the radiation source.

2. The radiation shield assembly of claim 1, wherein the first generally planar vertical shield is configured to be positioned such that a top edge of the first generally planar vertical shield is at least 175 cm (±20%) from the floor.

3. The radiation assembly of claim 1, wherein the first generally planar vertical shield is configured to be positioned such that a top edge of the first generally planar vertical shield is at least about the height of an adult human above the floor.

4. The radiation assembly of claim 1, wherein the first generally planar vertical shield has a height of at least about the distance from the upper surface of the table to an average human's full height.

5. The radiation assembly of claim 1, wherein the first generally planar vertical shield is fastened to the support arm and the second generally planar vertical shield is fastened to the support arm.

6. The radiation assembly of claim 1, wherein the support arm is configured to translate the radiation shield assembly relative to the table.

7. The radiation assembly of claim 1, wherein the support arm is supported from overhead.

8. The radiation assembly of claim 1, wherein in operation the support arm supports the entire weight of the radiation shield assembly.

9. The radiation assembly of claim 1, wherein at least one of the first generally planar vertical shield and the second generally planar vertical shield are configured to translate along the support arm.

10. The radiation assembly of claim 1, configured to position the first generally planar vertical shield and the second generally planar vertical shield to protect the user's head from radiation emanating from the radiation source.

11. The radiation assembly of claim 1, wherein at least one of the first generally planar vertical shield and the second generally planar vertical shield is configured to translate along the support arm.

12. The radiation assembly of claim 1, wherein the support arm is configured to position the first generally planar vertical shield and the second generally planar vertical shield to protect the user's upper body from the radiation emanating from the radiation source.

13. The radiation assembly of claim 1, wherein one or both of said shields have a radiopacity of at least 0.5 mm lead equivalent.

14. The radiation assembly of claim 1, further comprising a third generally planar shield fastened to the first generally planar vertical shield.

15. The radiation assembly of claim 14, wherein the third generally planar shield is translationally static with respect to the first generally planar vertical shield.

16. The radiation assembly of claim 1, wherein both of said shields reduce radiation exposure to no more than about 2.5 mR/hr when measured by the Modified ASTM F3094/IEC 61131-1 Protocol.

17. A radiation shield assembly, configured to block radiation emanating from a radiation source from below a table for supporting a patient, the assembly comprising:
(a) a support arm configured to be suspended from overhead, the support arm configured to support about the entire weight of the shield assembly;
(b) a first generally planar vertical shield that has a radiopacity to X-rays of at least 0.5 mm lead equivalent;
(c) a second generally planar vertical shield that has a radiopacity to X-rays of at least 0.5 mm lead equivalent; and
(d) at least one of: (i) a first sterile covering on the first generally planar vertical shield; and (ii) a second sterile covering on the second shielding means;
wherein the first generally planar vertical shield is joined to the second generally planar vertical shield to form a radiopaque barrier;
wherein the radiation shield assembly is configured to allow at least one of the first generally planar vertical shield and the second generally planar vertical shield to be rotated relative to the other about an approximately vertical axis; and
wherein the radiation shield assembly is configured to position the first generally planar vertical shield and the second generally planar vertical shield to protect a user's upper body from radiation emanating from the radiation source.

18. A radiation shield assembly, configured to block radiation emanating from a radiation source below a table for supporting a patient, the assembly comprising:
(a) a supporting means to support the assembly, and configured to allow the assembly to translate relative to the table to provide access to the patient;
(b) a first shielding means to block radiation from the source in a first approximately vertical plane, fastened to the supporting means, and
(c) a second shielding means to block radiation from the source in a second approximately vertical plane, fastened to the supporting means to allow the second shielding means to translate and rotate along an approximately vertical axis relative to the first shielding means;
(d) at least one of: (i) a first sterile covering on the first shielding means, and (ii) a second sterile covering on the second shielding means;
wherein the support means is configured to position the assembly such that a bottom edge of the first shielding means is about at the surface of the table and that a top edge of the first shielding means is at least 175 cm (±20%) from the floor.

19. The radiation shield assembly of claim 18, wherein the first and the second shielding means are configured to rotate relative to one another over an arc of from about 0-180°.

20. The radiation shield assembly of claim 18, wherein the supporting means comprises an approximately vertical mast.

21. The radiation shield assembly of claim 18, wherein in operation the supporting means supports the entire weight of the radiation shield assembly.

22. The radiation shield assembly of claim 18, wherein at least one of the first and second shielding means has a radiopacity of least 0.5 mm lead equivalent.

23. The radiation shield assembly of claim 18, wherein at least one of the first and second shielding means has a radiopacity of least 3 mm lead equivalent.

24. The radiation shield assembly of claim 18, wherein at least one of the first and second shielding means reduce radiation exposure by at least 85% when measured by the Modified ASTM F3094/IEC 61331-1 Protocol.

25. The radiation shield assembly of claim 18, wherein at least one of the first and second shielding means reduce radiation exposure to below 2.5 mR/hr when measured by the Modified ASTM F3094/IEC 61331-1 Protocol.

26. The radiation shield assembly of claim 18, wherein the support means comprises a mast supported by a floor stand.

27. The radiation shield assembly of claim 18, wherein the support means is a mast that is suspended by an overhead boom.

28. The radiation shield assembly of claim 18, wherein the support means is configured to position the assembly such that a bottom edge of the first shielding means is about at the surface of the table and that a top edge of the first shielding means is at least about 190 (±20%) cm from the floor.

29. A radiation shield assembly, configured to block radiation emanating from a radiation source below a table for supporting a patient, the radiation shield assembly comprising:
(a) a first generally vertical shield supported by a support member; and
(b) a second generally vertical shield supported by the support member; wherein the first and the second generally vertical shields can be rotated relative to one another about an axis approximately parallel to a longitudinal axis of the support member; and
(d) at least one of: (i) a first sterile covering on the first generally vertical shield, and (ii) a second sterile covering on the second generally vertical shield;
wherein the first and the second generally vertical shields have a height of at least a distance from an upper surface of the table to 175 cm (±10%) from a floor.

30. The radiation shield assembly of claim 29, wherein the first and the second generally vertical shields can be rotated relative to one another over an arc of at least about 90°.

31. The radiation shield assembly of claim 29, wherein the support member is capable of supporting an entire weight of the radiation shield assembly.

32. The radiation shield assembly of claim 29, wherein at least one of the first and second generally vertical shields has a radiopacity of least 0.5 mm lead equivalent.

33. The radiation shield assembly of claim 29, wherein the first and the second generally vertical shields can be rotated relative to one another about the longitudinal axis of the support member.

34. The radiation shield assembly of claim 29, wherein the support member is a mast that is suspended by an overhead boom.

35. The radiation shield assembly of claim 29, wherein the support member is configured to be supported by a ceiling.

36. The radiation shield assembly of claim 29, wherein the first generally vertical shield is fastened to the support member via a first radiopaque joint.

37. A radiation shield assembly, configured to block radiation emanating from a radiation source below a table for supporting a patient, the radiation shield assembly comprising:
(a) a first generally vertical shield supported by a support member;
(b) a second generally vertical shield supported by the support member; and
(d) at least one of: (i) a first sterile covering on the first generally vertical shield, and (ii) a second sterile covering on the second generally vertical shield;
wherein the first and the second generally vertical shields can be rotated relative to one another about an axis approximately parallel to a longitudinal axis of the support member;
and wherein the assembly is configured to position the first and the second generally vertical shields to protect a user's upper body from radiation emitted from said radiation source.

38. The radiation shield assembly of claim 37, wherein the assembly is configured to position the first and the second generally vertical shields at least 175 cm (±20%) above a floor below the table.

39. The radiation shield assembly of claim 37, wherein the first and the second generally vertical shields can be rotated relative to one another over an arc of at least 90°.

40. The radiation shield assembly of claim 37, wherein the support member is capable of supporting an entire weight of the radiation shield assembly.

41. The radiation shield assembly of claim 37, wherein at least one of the first and the second generally vertical shields has a radiopacity of least 0.5 mm lead equivalent.

42. The radiation shield assembly of claim 37, wherein the first generally vertical shield is fastened to the support member via a first radiopaque joint.

43. The radiation shield assembly of claim 37, wherein the support member is configured to be supported from overhead.

44. The radiation shield assembly of claim 37, wherein the first and the second generally vertical shields can be rotated relative to one another about the longitudinal axis of the support member.

45. A radiation shield assembly, configured to block radiation emanating from a radiation source below a table for supporting a patient, the radiation shield assembly comprising:
(a) a first generally vertical shield supported by a support member;
(b) a second generally vertical shield supported by the support member; wherein the first and the second generally vertical shields can be rotated relative to one another about an axis approximately parallel to a longitudinal axis of the support member; and
(d) at least one of: (i) a first sterile covering on the first generally vertical shield, and (ii) a second sterile covering on the second generally vertical shield;
wherein the radiation shield assembly is configured to position the first and the second generally vertical shields to extend from about a surface of the table to a level effective to prevent direct radiation from said source from reaching a user's head.

46. The radiation shield assembly of claim 45, wherein the first and the second generally vertical shields can be rotated relative to one another over an arc of at least 90°.

47. The radiation shield assembly of claim 45, wherein the support member is capable of supporting an entire weight of the radiation shield assembly.

48. The radiation shield assembly of claim 45, wherein at least one of the first and the second generally vertical shields has a radiopacity of least 0.5 mm lead equivalent.

49. The radiation shield assembly of claim 45, wherein the support member is a mast that is suspended from overhead.

50. The radiation shield assembly of claim 45, wherein the first generally vertical shield is fastened to the support member via a first radiopaque joint.

51. A radiography method comprising:
(a) positioning the radiation shield assembly of claim 1 between a patient and the user; and
(b) irradiating the patient using the radiation source positioned such that radiation passes at least partially through the patient while being blocked from reaching the user's upper body by the radiation shield assembly.

52. A radiography method comprising:
(a) positioning the radiation shield assembly of claim 17 between a patient and the user; and
(b) irradiating the patient using the radiation source positioned such that radiation passes at least partially through the patient while being blocked from reaching the user's upper body by the radiation shield assembly.

53. A radiography method comprising:
(a) positioning the radiation shield assembly of claim 18 between a patient and the user; and
(b) irradiating the patient using the radiation source positioned such that radiation passes at least partially through the patient while being blocked from reaching the user's upper body by the radiation shield assembly.

54. A radiography method comprising:
(a) positioning the radiation shield assembly of claim 29 between a patient and the user; and
(b) irradiating the patient using the radiation source positioned such that radiation passes at least partially through the patient while being blocked from reaching the user's upper body by the radiation shield assembly.

55. A radiography method comprising:
(a) positioning the radiation shield assembly of claim 37 between a patient and the user; and
(b) irradiating the patient using the radiation source positioned such that radiation passes at least partially through the patient while being blocked from reaching the user's upper body by the radiation shield assembly.

56. A radiography method comprising:
(a) positioning the radiation shield assembly of claim 45 between a patient and the user; and
(b) irradiating the patient using the radiation source positioned such that radiation passes at least partially through the patient while being blocked from reaching the user's upper body by the radiation shield assembly.

\* \* \* \* \*